United States Patent [19]
Binder et al.

[11] Patent Number: 6,156,179
[45] Date of Patent: Dec. 5, 2000

[54] COMPUTER DIRECTED IDENTIFICATION OF PARAPROTEINS

[75] Inventors: Steven R. Binder, Berkeley; Bryan H. Ikeda, Alameda; Caroline Scolari, Albany, all of Calif.

[73] Assignee: Bio-Rad Laboratories, Hercules, Calif.

[21] Appl. No.: 09/112,725

[22] Filed: Jul. 9, 1998

[51] Int. Cl.[7] .................................................. G01N 27/26
[52] U.S. Cl. .......................... 204/461; 436/86; 436/513; 436/516; 436/535
[58] Field of Search ..................................... 204/450, 451, 204/461, 600, 606; 436/86, 513, 516, 535; 435/4, 7.1

[56] References Cited

U.S. PATENT DOCUMENTS

| | | | |
|---|---|---|---|
| 4,668,363 | 5/1987 | Gebot et al. | 204/182.8 |
| 5,098,536 | 3/1992 | Anderson | 204/180.1 |
| 5,185,066 | 2/1993 | Golius | 204/182.8 |
| 5,228,960 | 7/1993 | Liu et al. | 204/451 |
| 5,443,952 | 8/1995 | Pestronk | 435/7.1 |
| 5,490,909 | 2/1996 | Wang et al. | 204/452 |
| 5,567,282 | 10/1996 | Wang et al. | 204/450 |
| 5,660,701 | 8/1997 | Grushka et al. | 204/451 |
| 5,736,330 | 4/1998 | Fulton | 435/6 |
| 5,932,080 | 8/1999 | Likuski | 204/451 |

FOREIGN PATENT DOCUMENTS

| | | |
|---|---|---|
| 62-032360 | 2/1987 | Japan . |
| 63 117 257 | 5/1988 | Japan . |

OTHER PUBLICATIONS

JAPIO abstract of Masato et al. (JP62032360 A), Feb. 1987.
D.W. Kirmse, et al., "Resolution Enhancement of chromatograph peaks," *Anal. Chem*, 43 (8):1035–1039 (Jul. 1971).
Aguzzi, et al., "<<Immunosubtraction>> Electrophoresis: A simple method for identifying specific proteins producing the cellulose acetate electrophoretogram," *Estratto dal. Boll 1st Sieroter* (Milanese), 56:212–216 (1977). Month Unknown.

M.L. Malczewski, et al., "Multiple peak recognition in high performance liquid chromatography by fast fourier transformation," *J. Chromatogr. Sci.*, 19:187–194 (Apr. 1981)
N.M. Papadopoulos, et al., "Incidence of ã–globulin banding in a healthy population by high–resolution electrophoresis," *Clin. Chem.*, 28(4):707–708 (1982). Month Unknown.
Merlini, "Identification of specific plasma proteins determining the agarose gel electrophoresis by the immunosubtraction technique," *J. Clin. Chem. Clin. Biochem.*, 21:841–844(1983). Month Unknown.
Lasters, et al., "Background estimation in one–dimensional electropherograms of whole–cell protein extracts," *Electrophoresis*, 6:508–511 (1985). Month Unknown.
C.A. Mancuso, et al., "A method for the separation and characterization of archaebacterial signature ether lipids," *Index Medicus* database record, *J. Announcement*: 8607 Jan. (1986). Abstract.
S.D. Aird, et al., "Comparative spectroscopic studies of four crotoxin homologs and their subunits," *Index Medicus* database record, *J. Announcement*: 8912 ( Aug. 31, 1989.) Abstract.
P.J. Cardot, et al., "A fully automated chromotographic peak detection and treatment software for multi–user multi–task computers," *Index Medicus* database record, *J. Announcement*: 9110 (1990). Month Unknown. Abstract.
J.Y. Yang, et al.,"An alternate apoprotein conformation in high density apolipoprotein discoidal complexes," *Index Medicus* database record, *J. Announcement*: 9207 (1991). Month Unknown. Abstract.

(List continued on next page.)

*Primary Examiner*—Jill Warden
*Assistant Examiner*—Alex Noguerola
*Attorney, Agent, or Firm*—Townsend and Townsend and Crew LLP

[57] ABSTRACT

The present invention is generally directed to the analysis of biological samples. More particularly, the present invention is directed to automated sample analysis for paraproteins using immunosubtraction, capillary electrophoresis and Fourier transformation analysis.

36 Claims, 33 Drawing Sheets

OTHER PUBLICATIONS

S. Millership, et al., "Automated lanes detection and comparison of bacterial electrophoretic protein fingerprints using fast, fourier transformation, "*Computers and Biomedical Research,* 25:392–406 (1992). Month Unknown.

M.A.A. Kratzer, et al., "Neuronal network analysis of serum electrophoresis," *J. Clin. Pathol* 45: 612–615 (1992). Month Unknown.

H. Cren, et al., "Use of automated smoothing and deconvolution procedures for the determination of human breast cancer estrogen and progesterone receptor isoforms, after high–performance size–exclusion chromatography, " *Index Medicus* database record, *J. Announcement*: 9311 (May 19, 1993).

G. Bonnot, et al., "Fourier processing of liquid chromatograms using flow radioactive detection," *Index Medicus* database record, *J. Announcement*: 9507 ( Jan.1,1995 ).

K.A. Barbee, et al., "Deconvolution of gel filtration chromotographs of human plasma lipoproteins, "*Anal. Biochem,* 231:301–308 (1995). Month Unknown.

M. Ivandić et al., "Development and evaluation of a urine protein expert system," *Clin. Chem.*, 42(8):1214–1222 (1996).

J.Bienvenu, et al., "Multicenter evaluation of the paragon CZE™ 2000 capillary zone electrophoresis system for serumprotein electrophoresis and monoclonal component typing," *Clin. Chem.*, 44(3):599–605 (1998). Month Unknown.

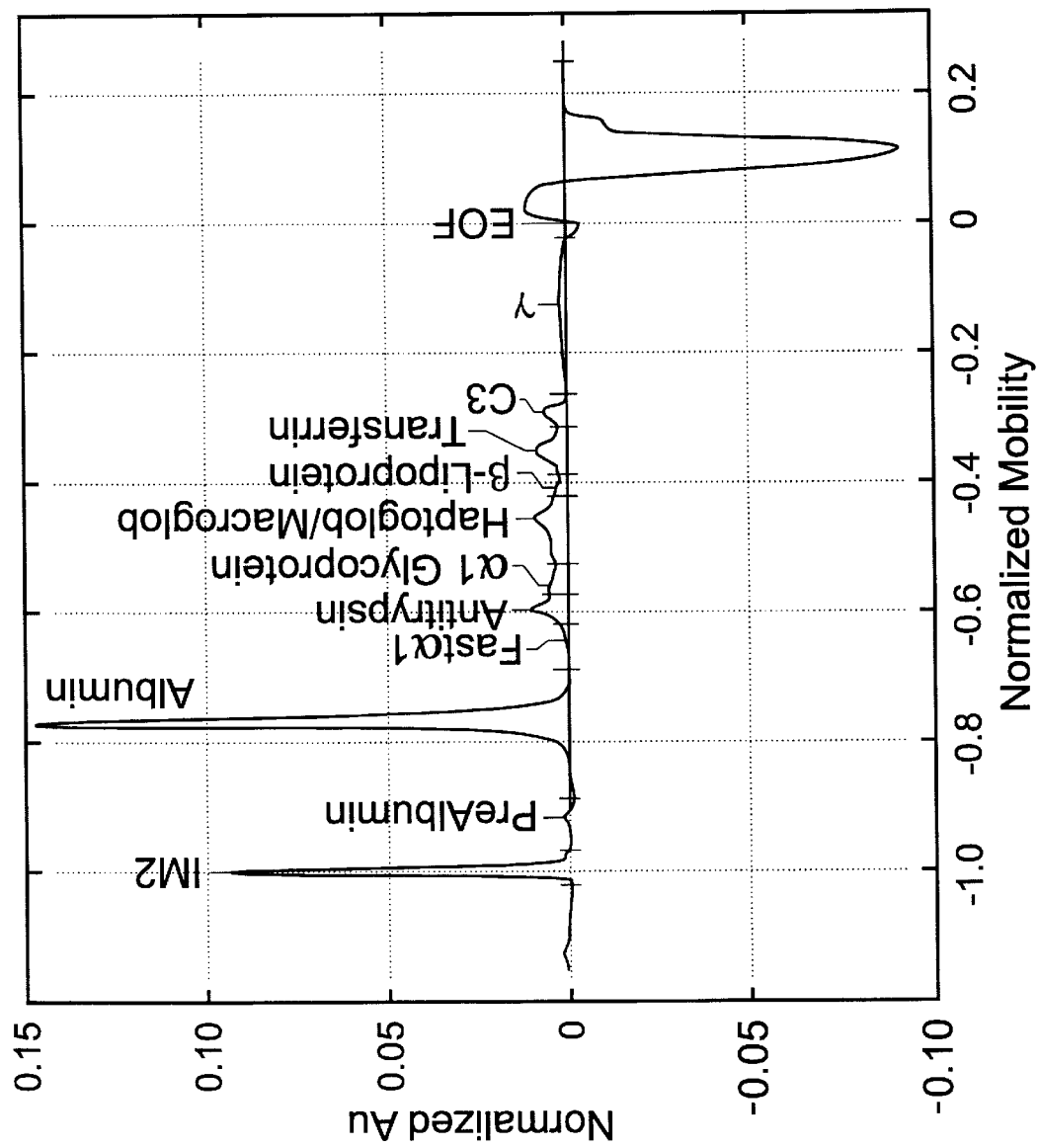

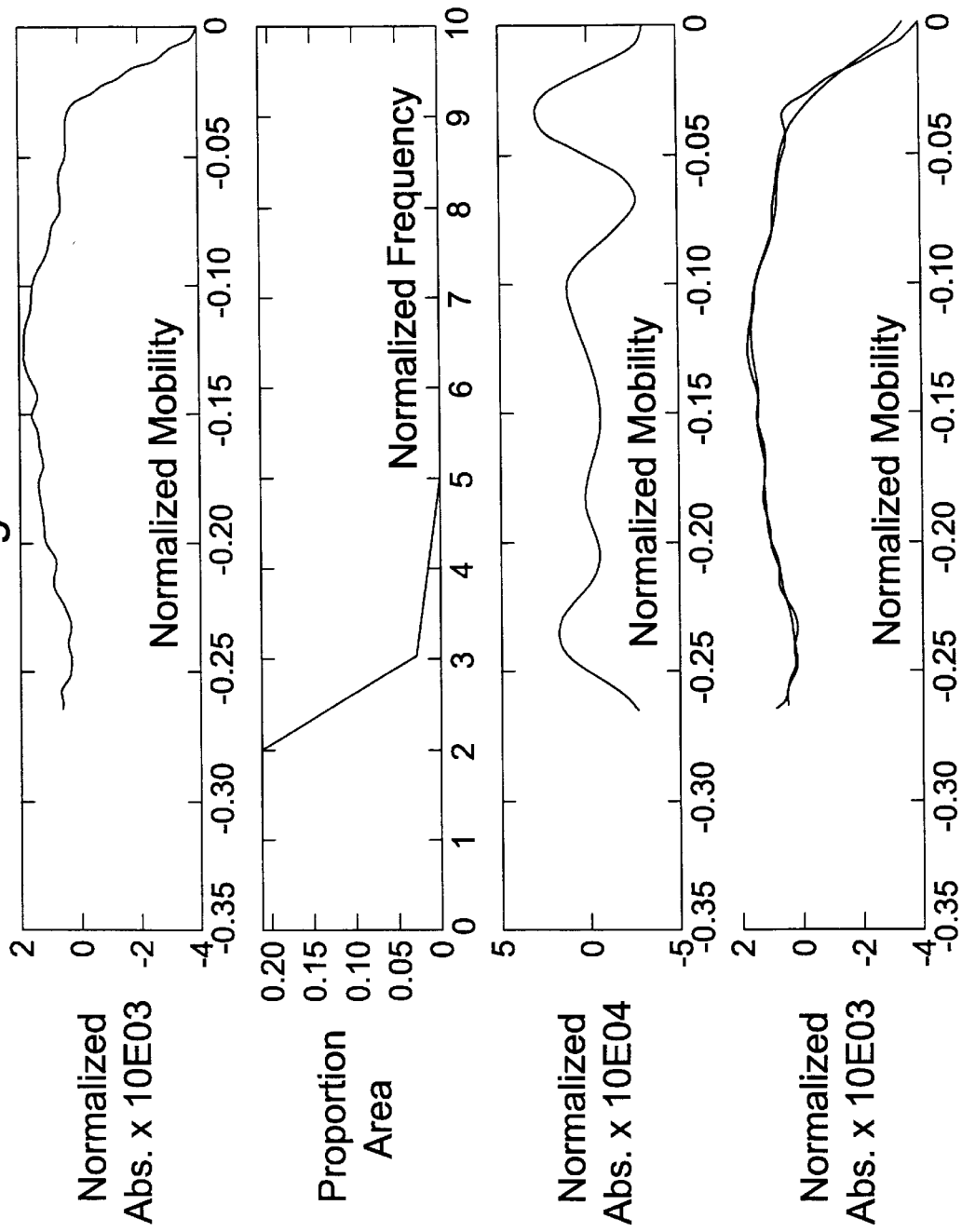

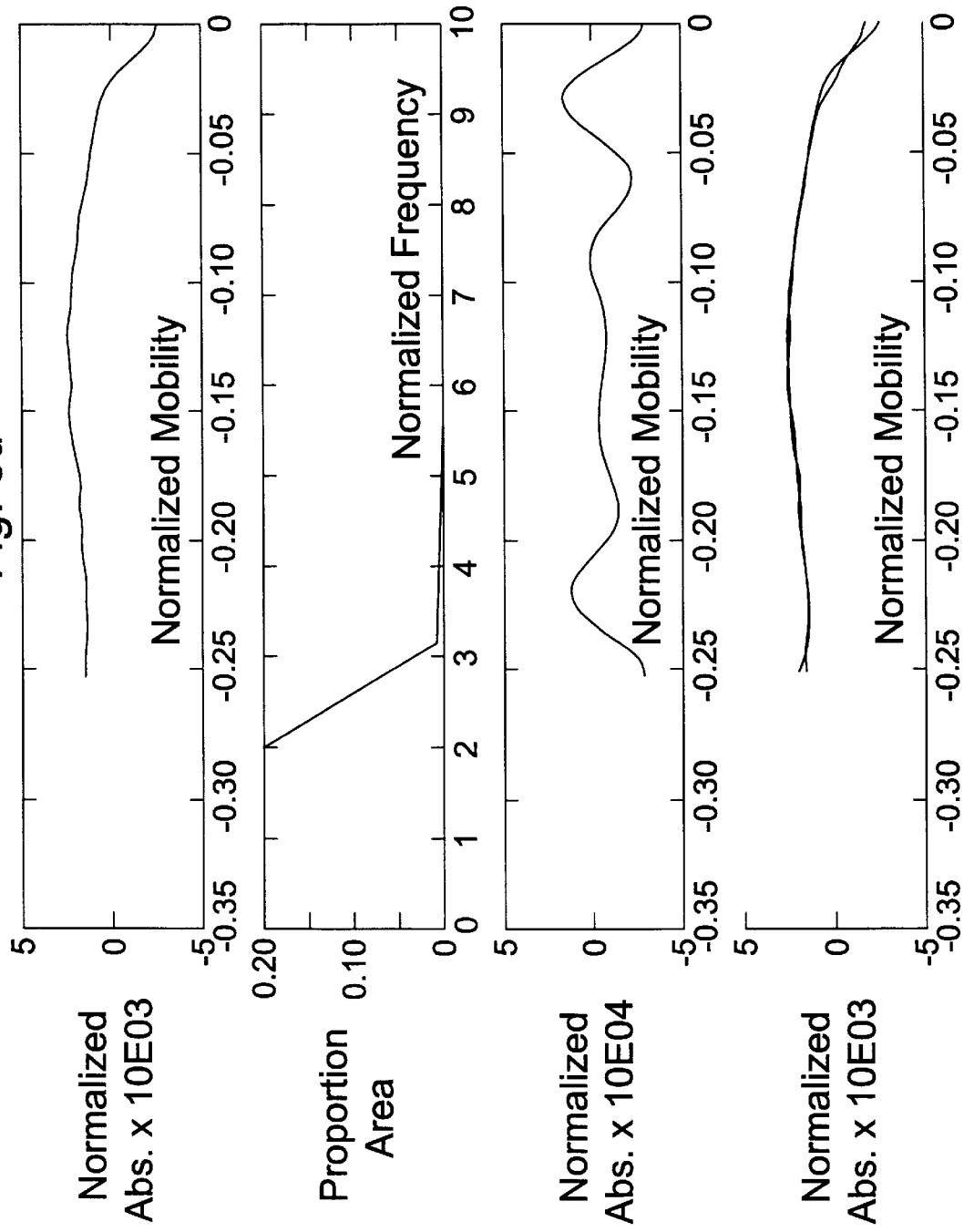

Fig. 4a

EXAMPLE 1: Small Paraprotein Response Superposed on a Normal Serum Protein Response

<u>Sample BJ5 - Two Features Selected for Examination by User</u>
  Feature 1 at -0.0930 IgG, Lambda
  Feature 2 at -0.1210 Crest of Gamma Region, Not a Paraprotein

Feature 1 Analysis Summary

| Treatment | Check Region | Feature Found | Feature Y (AU) | Proportion Characteristic Area | Absolute Characteristic Area | Treatment Result |
|---|---|---|---|---|---|---|
| IgG + IgA | - | No | | | | - |
| IgG + IgM | - | No | | | | - |
| Kappa | + | Yes | 0.0028 | 5.138E-003 | 8.819E-006 | + |
| Lambda | - | No | | | | - |

Analysis ID: IdG, Lambda at -0.0930 Normalized Mobility Units

Fig. 4b

Feature 2 Analysis Summary

| Treatment | Check Region | Feature Found | Feature Y (AU) | Proportion Characteristic Area | Absolute Characteristic Area | Treatment Result |
|---|---|---|---|---|---|---|
| IgG + IgA | - | No | | | | - |
| IgG + IgM | - | No | | | | - |
| Kappa | + | No | | | | - |
| Lambda | - | No | | | | - |

Analysis ID: No Assignment

Analysis Thresholds for Significant Removal of Paraprotein

Proportion Characteristic Frequency Area Multiplicative Threshold   1.4662E-003
Proportion Characteristic Frequency Area Additive Threshold   8.7744E-003
Absolute Characteristic Frequency Area Multiplicative Threshold   9.0937E-006
Absolute Characteristic Frequency Area Additive Threshold   ----
Feature Height Multiplicative Threshold   0.0006
Feature Height Additive Threshold   ----

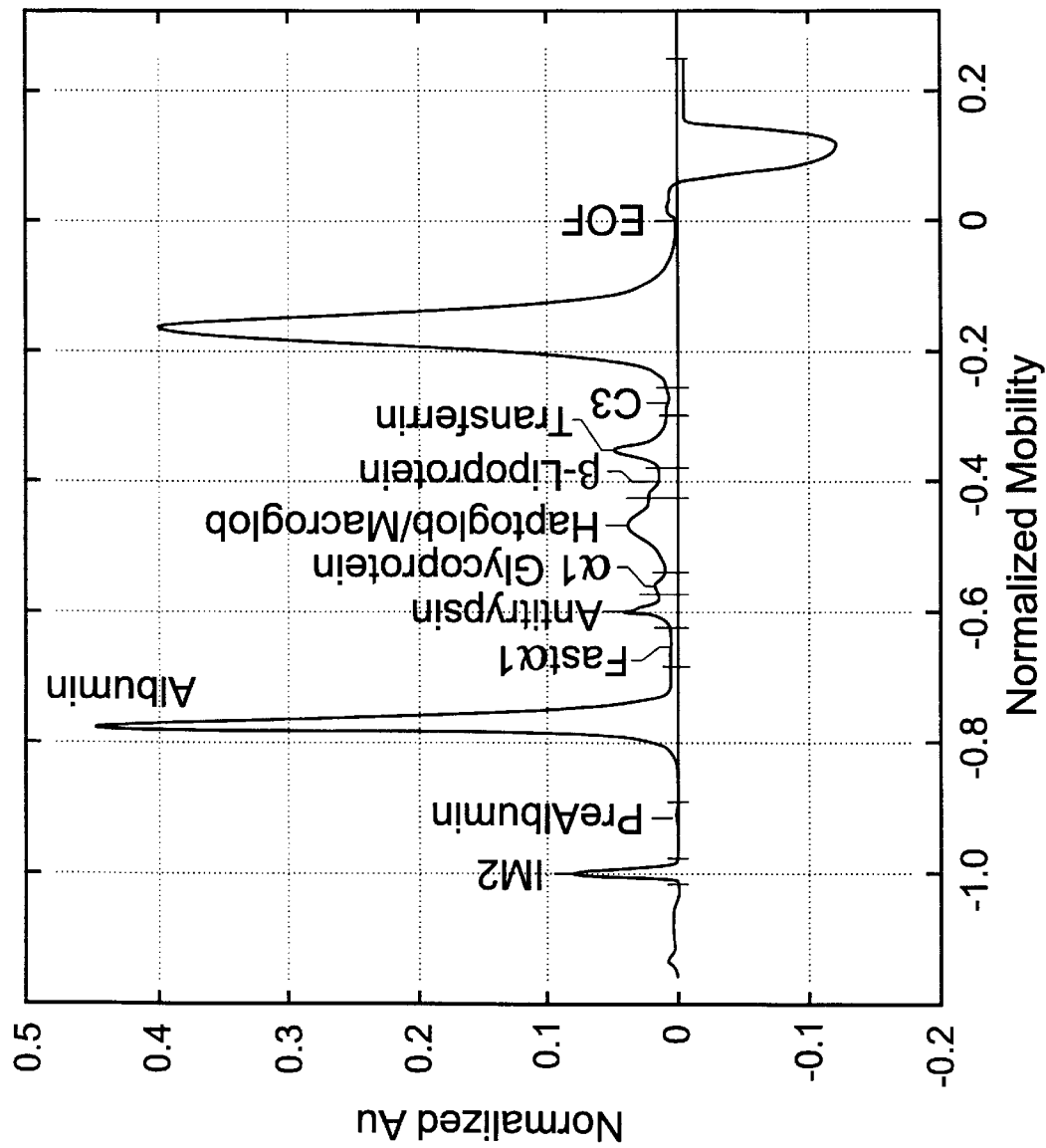

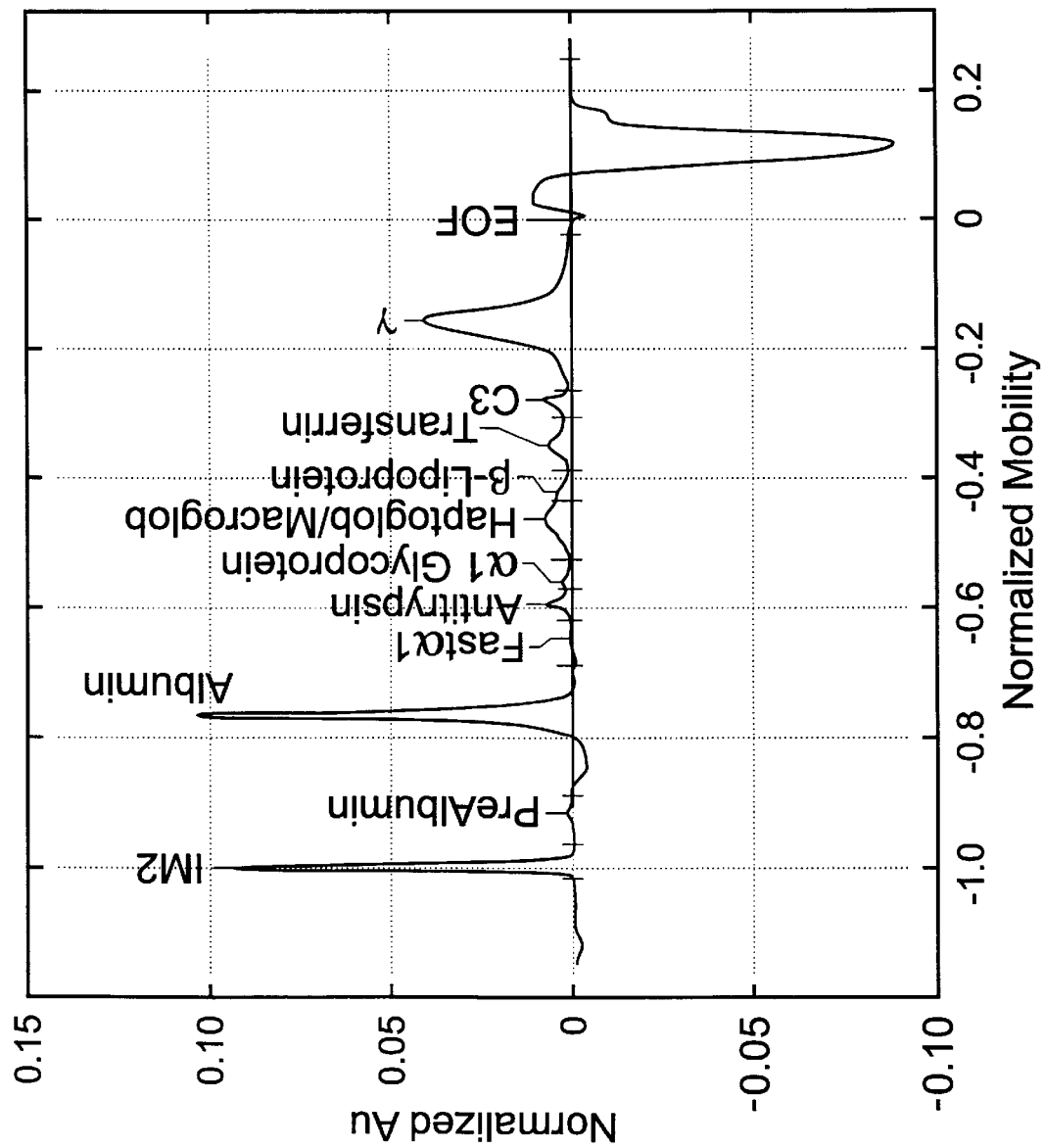

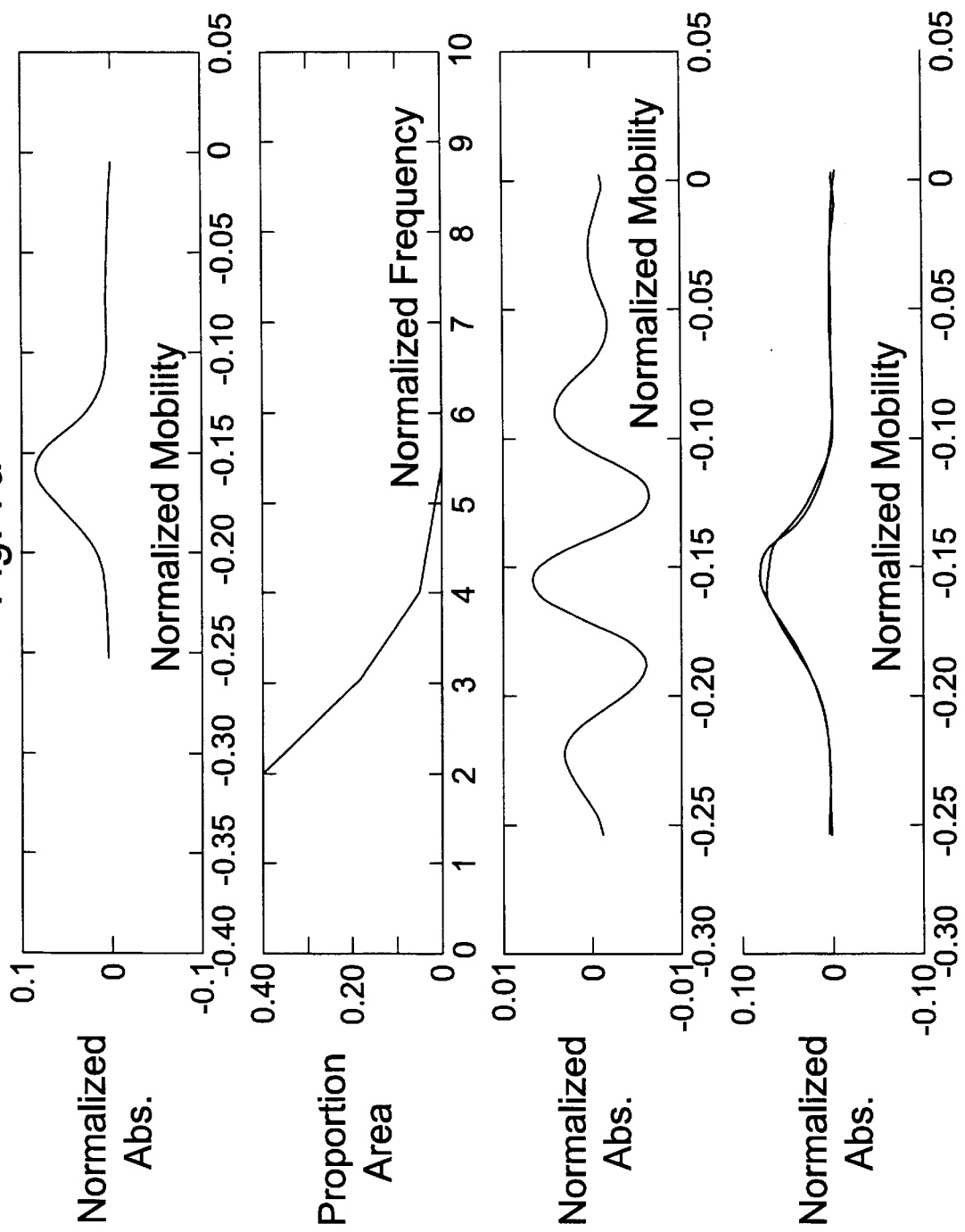

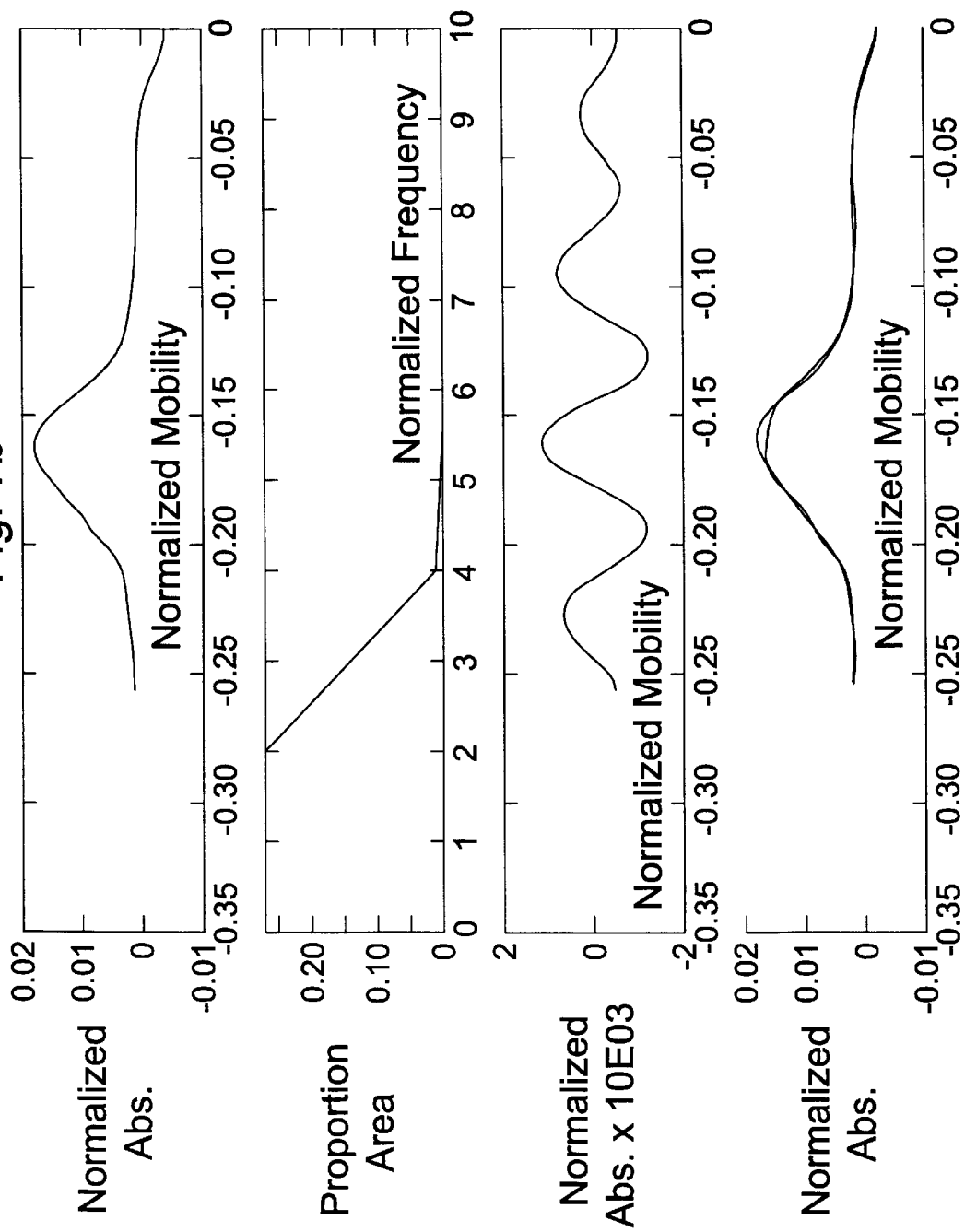

Fig. 8a

EXAMPLE 2: Large Paraprotein Response

SAMPLE BJ7 - One Feature Selected for Examination by User
Feature 1 at -0.1600 IgM, Kappa

Feature 1 Analysis Summary

| Treatment | Check Region | Feature Found | Feature Y (AU) | Proportion Characteristic Area | Absolute Characteristic Area | Treatment Result |
|---|---|---|---|---|---|---|
| IgG + IgA | + | Yes | 0.0805 | 0.03810 | 8.779E-003 | + |
| IgG + IgM | + | Yes | 0.0183 | 0.01978 | 2.827E-004 | - |
| Kappa | + | Yes | 0.0424 | 0.03217 | 2.092E-003 | - |
| Lambda | + | Yes | 0.0860 | 0.03445 | 9.076E-003 | + |

Analysis ID: IgM, Kappa at -0.1600 Normalized Mobility Units

*Fig. 8b*

Analysis Thresholds for Significant Removal of Paraprotein

| | |
|---|---|
| Proportion Characteristic Frequency Area Multiplicative Threshold | 5.7154E-003 |
| Proportion Characteristic Frequency Area Additive Threshold | ---- |
| Absolute Characteristic Frequency Area Multiplicative Threshold | 4.5317E-003 |
| Absolute Characteristic Frequency Area Additive Threshold | ---- |
| Feature Height Multiplicative Threshold | 0.0688 |
| Feature Height Additive Threshold | ---- |

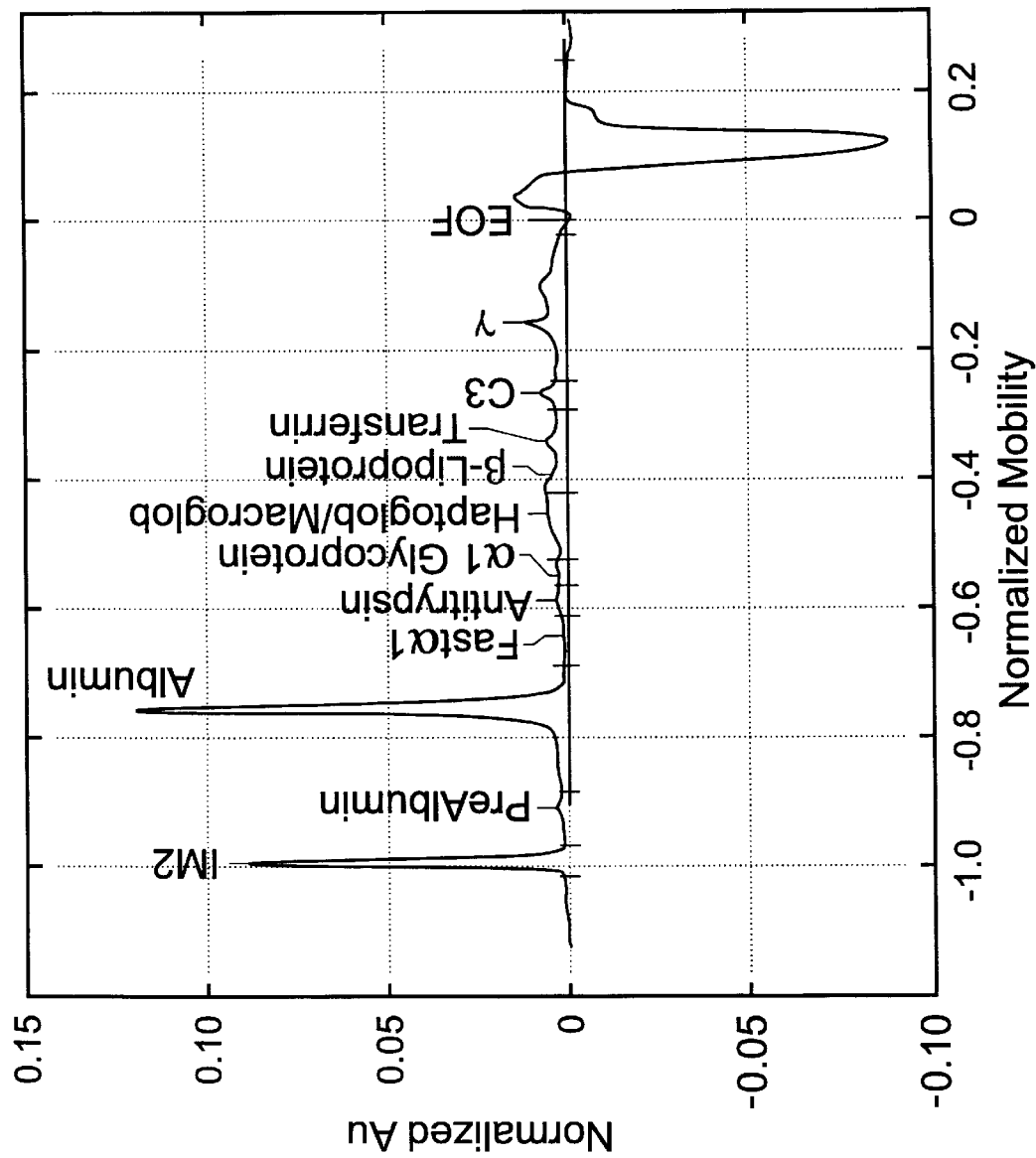

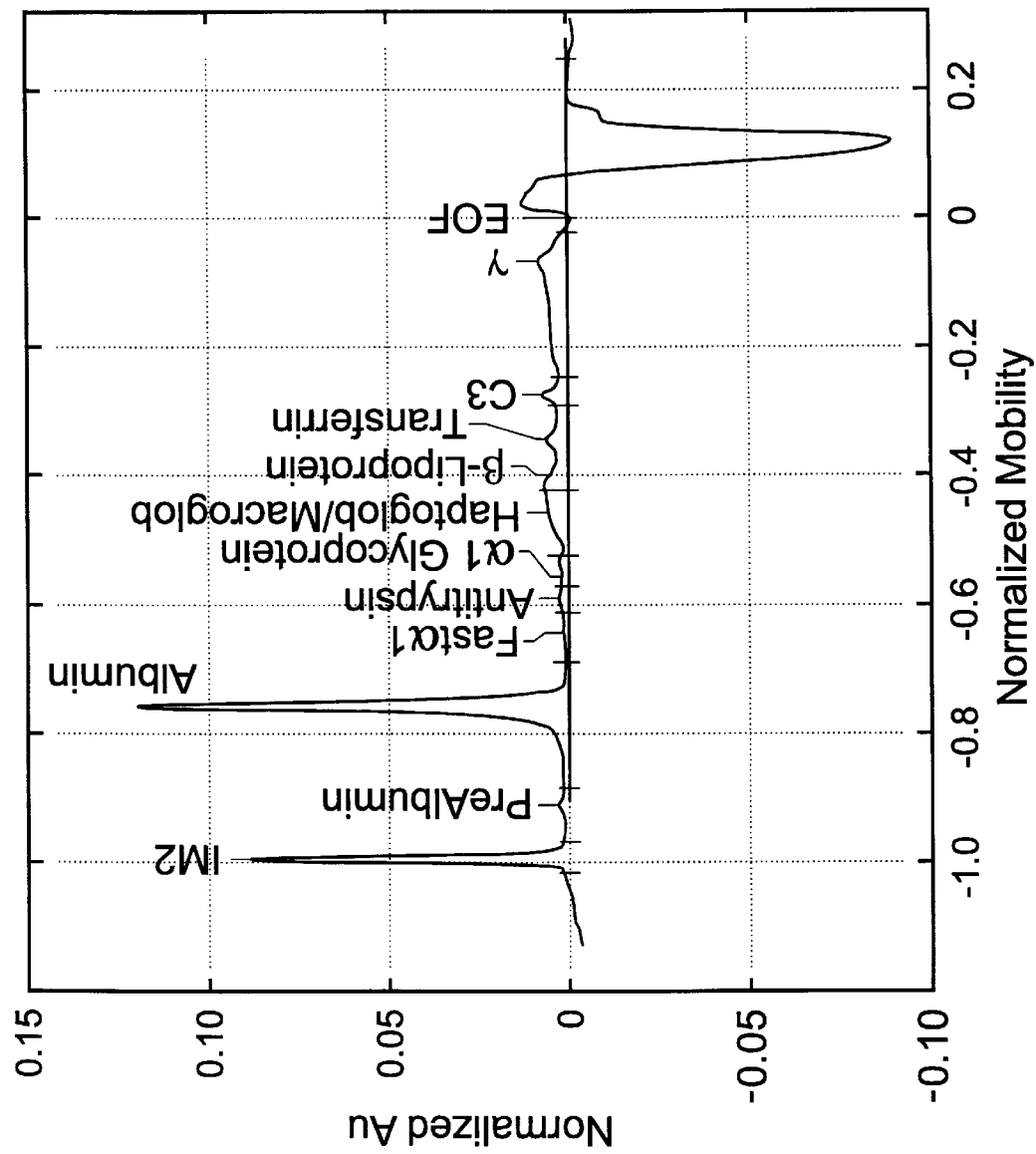

*Fig. 12a*

EXAMPLE 3: Two Paraproteins in a Single Region

Sample BFI2 - Two Features Selected for Examination by User
Feature 1 at -0.0700 IgG, Kappa
Feature 2 at -0.1200 IgG, Lambda

Feature 1 Analysis Summary

| Treatment | Check Region | Feature Found | Feature Y (AU) | Proportion Characteristic Area | Absolute Characteristic Area | Treatment Result |
|---|---|---|---|---|---|---|
| IgG + IgA | - | No | | | | - |
| IgG + IgM | - | No | | | | - |
| Kappa | + | No | | | | - |
| Lambda | + | Yes | 0.0088 | 5.458E-003 | 2.731E-005 | + |

Analysis ID: IgG, Kappa at -0.070 Normalized Mobility Units

*Fig. 12b*

Feature 2 Analysis Summary

| Treatment | Check Region | Feature Found | Feature Y (AU) | Proportion Characteristic Area | Absolute Characteristic Area | Treatment Result |
|---|---|---|---|---|---|---|
| IgG + IgA | - | No | | | | - |
| IgG + IgM | - | No | | | | - |
| Kappa | + | Yes | 0.0077 | 2.184E-002 | 7.325E-005 | + |
| Lambda | + | No | | | | - |

Analysis ID: IgG, Lambda at -0.120 Normalized Mobility Units

Analysis Thresholds for Significant Removal of Paraprotein

Proportion Characteristic Frequency Area Multiplicative Threshold    3.2764E-003
Proportion Characteristic Frequency Area Additive Threshold    ----
Absolute Characteristic Frequency Area Multiplicative Threshold    3.6625E-005
Absolute Characteristic Frequency Area Additive Threshold    ----
Feature Height Multiplicative Threshold    0.0061
Feature Height Additive Threshold    ----

COMPUTER DIRECTED IDENTIFICATION OF PARAPROTEINS

REFERENCE

This application is related to commonly owned and U.S. application Ser. No. 08/895,247 filed Jul. 21, 1997, which is now U.S. Pat. No. 5,922,184, entitled "Computer Directed Detection of Paraproteins," by Steven R. Binder et al., the teachings of which are incorporated herein by reference.

FIELD OF INVENTION

The present invention is generally directed to the analysis of biological samples. More particularly, the present invention is directed to automated protein analysis for abnormal proteins using immunosubtraction, capillary electrophoresis and Fourier analysis.

BACKGROUND OF THE INVENTION

The detection, identification and quantitation of paraproteins is useful for the detection of multiple myeloma. Monitoring paraprotein production is a necessary aspect to treat such diseases. Those suffering from multiple myeloma will produce one or more abnormal immunoglobulins or paraproteins which, if detected at an early stage, allows an aggressive treatment plan to be employed. Left undetected, a more extreme therapy can be required. Thus, it is important to properly detect paraproteins at as low a level as possible.

Detection of paraproteins may be performed using gel electrophoresis or capillary electrophoresis. In gel electrophoresis, the stained gel generally contains a pattern consisting of a series of dark bands on a light background. This gel response is then visually examined for abnormalities. A gel densitometric trace may also be obtained and used. The gel densitometric trace records the absorbance of the gel at a series of x positions on the gel, using a particular detection wavelength. This trace is useful for quantitation of results.

In capillary electrophoresis, the sample response usually consists of the absorbance of the proteins as they flow past the detector. Capillary electrophoresis has the advantage that separations can be performed in relatively short periods of time by using high voltages, since the small diameter and thin wall of the capillary provide efficient removal of the joule heat generated by the voltage. The capillary electrophoresis measurement is also more readily automated. Typically UV absorbance detection is used for detection of the proteins, with no staining step required.

A response with an x-axis of migration time is typically the data obtained from the capillary electrophoresis experiment. An x-axis that has been shown to give more precise identification and quantitation of electropherogram components is normalized mobility (see, co-pending U.S. application Ser. No. 08/866,282, Likuski, R. K., "Mobility and Normalized Capillary Electrophoresis," incorporated herein by reference). The migration time axis can be changed to normalized mobility by: 1) taking the reciprocal of migration time; 2) multiplying by an appropriate constant; 3) zero correcting by subtracting the electroosmotic velocity; 4) dividing by the zero corrected mobility of a charged marker; and 5) multiplying by a constant, preferably −1. The appearance of this normalized data set also more closely resembled that of the analogous gel electrophoresis densitometer trace, a shape that is familiar to clinicians.

It is common practice to identify or type a paraprotein by its heavy chain and light chain constituent parts. A typical antibody or immunoglobulin consists of a pair of two "heavy" chains linked to a pair of two identical "light" chains to form a hypothetical "Y" structure. The heavy chains form the base of the "Y," and the light chains form the two branches. The heavy chains and light chains are separately synthesized by the immune system. There are two types of light chains, referred to as "kappa" ("κ") and "lambda" ("λ"). Similarly, there are several classes of heavy chains: γ ("IgG"); α "IgA"); δ ("IgD"); μ ("IgM") and ε ("IgE"). IgG, IgA and IgM are the major serum immunoglobulins; IgD and IgE are generally present in serum only at very low concentrations.

Immunofixation electrophoresis (IFE) has been the method of choice for the typing of paraproteins in gels. In IFE, several replicates of sample are subjected to electrophoresis. After gel separation of the components of interest, a different specific antibody is added to each sample replicate. The sample replicates are then allowed to bind to the different specific antibodies. The antibody-protein complex that forms is an insoluble precipitate. Unbound antibody and unreacted protein is then washed away, and the gel is stained, leaving a series of dark bands indicative of the identity of the components present in the original sample. IFE is a reliable, but time consuming and labor-intensive process that is more amenable to gel electrophoresis than capillary electrophoresis.

A related accepted method for the identification of paraproteins is the method of Aguzzi and Poggi (see, Aguzzi et al., "Immunosubtraction Electrophoresis: A Single Method for Identifying Specific Proteins Producing the Cellulose Acetate Electropherogram," Estratto dal. Boll $1^{st}$ Sieroter, Milanese 56/3:212–216 (1977) incorporated herein by reference). This method uses cellulose acetate sheets and/or strips. Some strips are left untreated, while others are constructed to contain a segment containing antibodies to sample components of interest near the point of sample application. Using their electrophoretic conditions, the antibodies contained in the constructed segment do not migrate significantly. Serum samples are applied to treated and untreated strips and electrophoresed. In the treated strips, the component of interest present in the sample binds to the appropriate antibody contained in the constructed segment, and the bound antibody-antigen complex precipitates. The component of interest does not migrate past this zone in the treated strips, while migrating normally in the untreated strips. The unbound sample components migrate normally on both treated and untreated strips, and appear in their expected locations. By comparison of the migration patterns of treated and untreated strips, the location of the component of interest can be found. The authors refer to this procedure as immunosubtraction.

The method of Aguzzi and Poggi has been used for the identification of paraproteins in capillary electrophoresis. A sample is first run, and paraprotein(s) visually detected. Antibodies to the components of interest (IgG, IgM, IgA, kappa and lambda) are coated onto beads or left free in solution (see, U.S. Pat. Nos. 5,228,960 and 5,567,282, incorporated herein by reference). The antibodies to the paraproteins, in essence anti-antibodies, are successively added to aliquots of the sample, one type of antibody per sample, causing removal of these components from the sample aliquot, or causing a shift in mobility of the component(s) of interest. These sample aliquots are then run by capillary electrophoresis, and the differences between the untreated and treated samples examined visually to determine the type of paraprotein originally present.

Prior to the discoveries underlying the present invention, methods for identification of paraproteins by immunosubtraction have relied on visual comparison of the differences between untreated and treated samples. Methods relying on visual comparison of results are inherently subjective, and require a time-consuming examination of each sample result. A large paraprotein response can be readily detected and identified visually, but smaller paraproteins can be more of a challenge. The reliability of the method varies with the expertise of the technician examining the immunosubtraction results. What is needed in the art is a process that performs this comparison in an automated fashion and provides a method that is more amenable to high throughput screening, and gives more consistent results. The present invention fulfills this and other needs.

SUMMARY OF THE INVENTION

In one aspect, this invention relates to an immunosubtraction method of analyzing a biological sample for the presence or absence of at least one constituent of interest; the method involves:

(a) mixing at least one aliquot of the biological sample with at least one specific binding partner that is capable of significantly removing at least one constituent of interest to generate a first treated sample;

(b) separating a portion of the first treated sample into constituent parts to generate a first data set; and (c) subjecting at least a portion of the first data set to a first analysis to generate a parameter set indicative of the at least one constituent of interest.

In an especially preferred embodiment, the method further includes:

(d) assigning a binary decision code to the first treated sample using the generated parameter set; and (e) comparing the binary decision code to a matrix of expected results to identify the constituent of interest.

The methods of this invention are of greatest interest for the analysis of biological samples, or the detection and/or quantifying of specific components in biological samples. Typical samples include, but are not limited to, whole blood, plasma, serum, urine and cerebrospinal fluid. Human serum is one of the most common samples in need of analysis.

In a preferred embodiment, the biological sample is a serum sample and the constituent of interest is a paraprotein. The separation to form the first data set is preferably accomplished by capillary electrophoresis. The x-axis of the first data set is preferably expressed in normalized mobility units. The parameter set is preferably generated using a Fourier analysis of the first data set. This parameter set can then be used to assign a binary decision code to the treated sample (either negative or positive). The binary decision codes from a panel of treated samples can then be used to identify the paraprotein present by comparing the assigned binary decision codes from a panel of treated samples to a matrix of expected results.

These and other features, benefits and advantages of the invention are explained in further detail below.

BRIEF DESCRIPTION OF THE DRAWINGS

FIGS. 2A–D are a set of four graphs which illustrate a first data set after separation of a panel of treated samples using the methods of the present invention; the x axis has units of normalized mobility, and the y axis has units of normalized absorbance. FIG. 2A is a sample response obtained after treatment with beads containing anti-IgG:anti-IgA immunoglobulins. FIG. 2B is a sample response after treatment with beads containing a mixture of anti-IgG:anti-IgM immunoglobulins. FIG. 2C is a sample response after treatment with beads containing anti-kappa immunoglobulin. FIG. 2D is a sample response after treatment with beads containing anti-lambda immunoglobulin.

FIGS. 3A–D are a set of four graphs which provide an illustration of the Fourier Analysis results from each of the individual sample treatments. FIGS. 3A–D show the final result of the analysis in the top subplot. A paraprotein feature was found in FIG. 3C, with no features being found in the other panel items. FIGS. 3A–D show the power spectrum generated in the second subplot, with the parameter proportion area specifically being plotted in this instance. FIGS. 3A–D show in the third subplot the back-transform of the data in the first subplot after it has been filtered to exclude the non-characteristic part. FIGS. 3A–D in the fourth subplot show the comparison between the original data and a back-transform of the non-characteristic part of the data.

FIGS. 4A and 4B illustrate the result obtained by running the sample panel from FIGS. 3A–D through the method of the present invention. The correct location of the feature was input to the algorithm, as well as a spurious location. The method correctly identified the identity of the component at −0.0930 normalized mobility units, i.e., IgG, lambda, and also correctly gave the result of "no assignment" for the spurious location.

FIG. 5 is a graph which shows a serum protein sample with a large paraprotein result in the gamma region, at a normalized mobility of approximately −0.16, which is known to be of type IgM, kappa.

FIGS. 6A–D are a set of four graphs showing a first data set from a panel of treated samples containing a large paraprotein, analyzed by the method of the present invention. The x axis has units of normalized mobility, and the y axis has units of normalized absorbance. FIG. 6A is a sample response obtained after treatment with beads containing a mixture of anti-IgG:anti-IgA immunoglobulins. FIG. 6B is a sample response obtained after treatment with beads containing a mixture of anti-IgG:anti-IgM immunoglobulins. FIG. 6C is a sample response obtained after treatment with beads containing anti-kappa. FIG. 6D is a sample response obtained after treatment with beads containing anti-lambda.

FIGS. 7A–D are a set of four graphs which provide an illustration of the Fourier Analysis results from each of the individual sample treatments. FIGS. 7A–D show the final result of the analysis in the top subplot. The feature of interest is found in all samples. FIGS. 7A–D show the power spectrum generated in the second subplot, with proportion area specifically being plotted in this instance. FIGS. 7A–D show in the third subplot the back-transform of the data in the first subplot after it has been filtered to exclude the non-characteristic part. FIGS. 7A–D, fourth subplot, shows the comparison between the original data and a back-transform of the non-characteristic part of the data.

FIGS. 8A and 8B illustrate the result obtained by running the sample panel from FIGS. 7A–D through the method of the present invention. The correct location of the feature was input to the algorithm. The method correctly identified the identity of the component at −0.16 normalized mobility units as IgM, kappa.

FIGS. 10A–D are a set of four graphs similar to FIGS. 2A–D, showing a first data set from a panel of treated samples containing two paraproteins of differing type, which is the data input into the method of the current invention. For the traces shown in this figure, the x axis has units of normalized mobility, and the y axis has units of normalized absorbance. FIG. 10A is a sample response obtained after treatment with beads containing a mixture of anti-IgG:anti-IgA immunoglobulins. FIG. 10B is a sample response obtained after treatment with beads containing a mixture of anti-IgG:anti-IgM immunoglobulins. FIG. 10C is a sample response obtained after treatment with beads containing anti-kappa. FIG. 10D is a sample response obtained after treatment with beads containing anti-lambda.

FIGS. 11A–D show the final result of the analysis in the top subplot. The only feature found in FIG. 11A results from a spike of undetermined origin. No paraprotein response is found in FIG. 11B. FIG. 11C again finds the spike of undetermined origin, along with the paraprotein at normalized mobility −0.12. FIG. 11D finds the spike of undetermined origin, and the paraprotein at normalized mobility −0.07. FIGS. 11A–D show the power spectrum generated in the second subplot, with proportion area specifically being plotted in this instance. FIGS. 11A–D show in the third subplot the back-transform of the data in the first subplot after it has been filtered to exclude the non-characteristic part. FIGS. 11A–D, fourth subplot, show the comparison between the original data and a back-transform of the non-characteristic part of the data.

FIG. 12A and 12B illustrate the result obtained by running the sample panel from FIGS. 11A–D through the method of the present invention. The correct feature locations were input to the algorithm. The method correctly identified the identity of the component at −0.07 normalized mobility units as IgG, kappa, and the identity of the component at −0.12 normalized mobility units as IgG, lambda.

DETAILED DESCRIPTION OF THE INVENTION AND PREFERRED EMBODIMENTS

Figure 1:
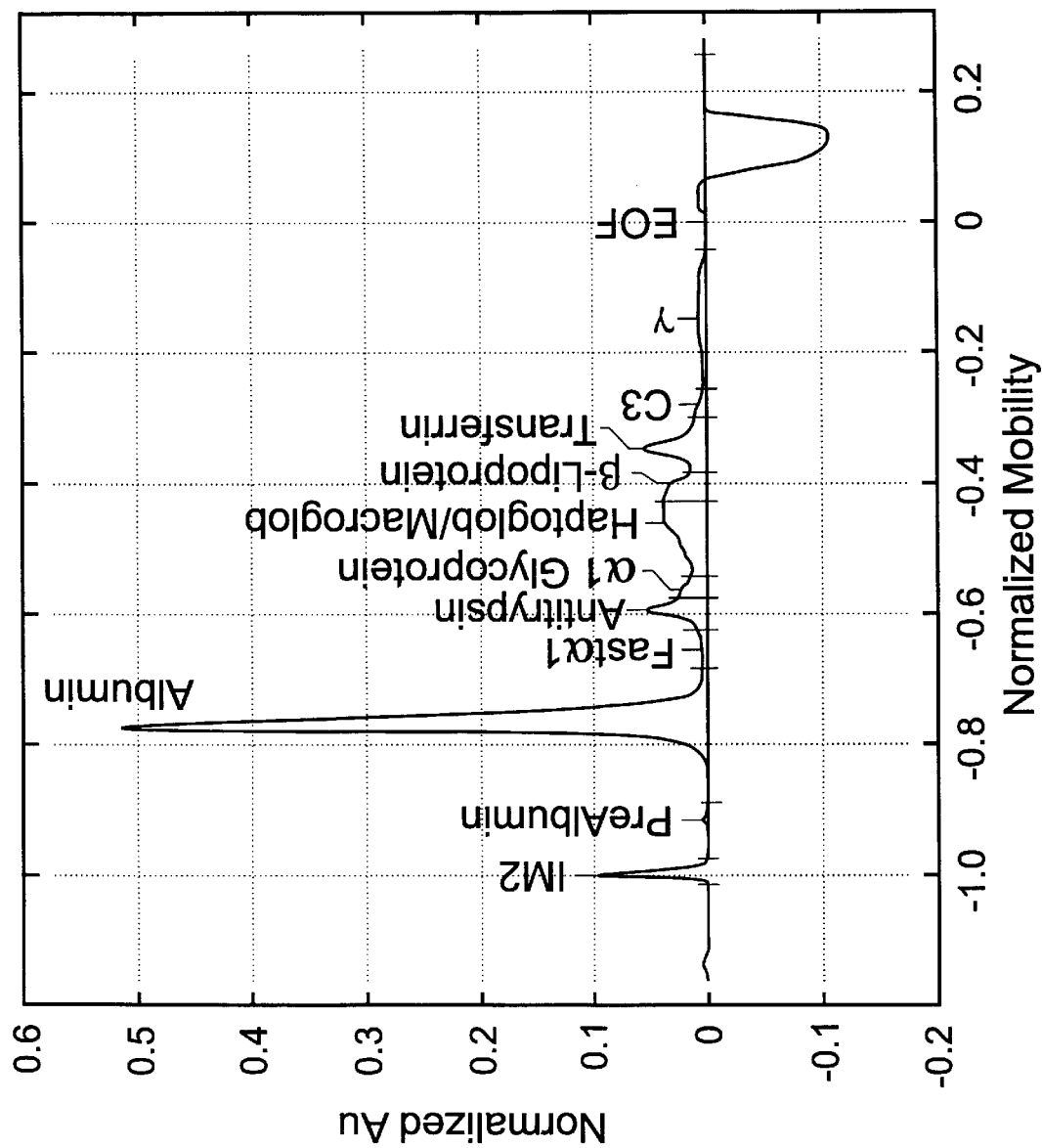
FIG. 1 is a graph which shows a serum protein sample with a small paraprotein result in the gamma region, at a normalized mobility of approximately −0.093, which is known to be of type IgG, lambda.
Figure 2A:
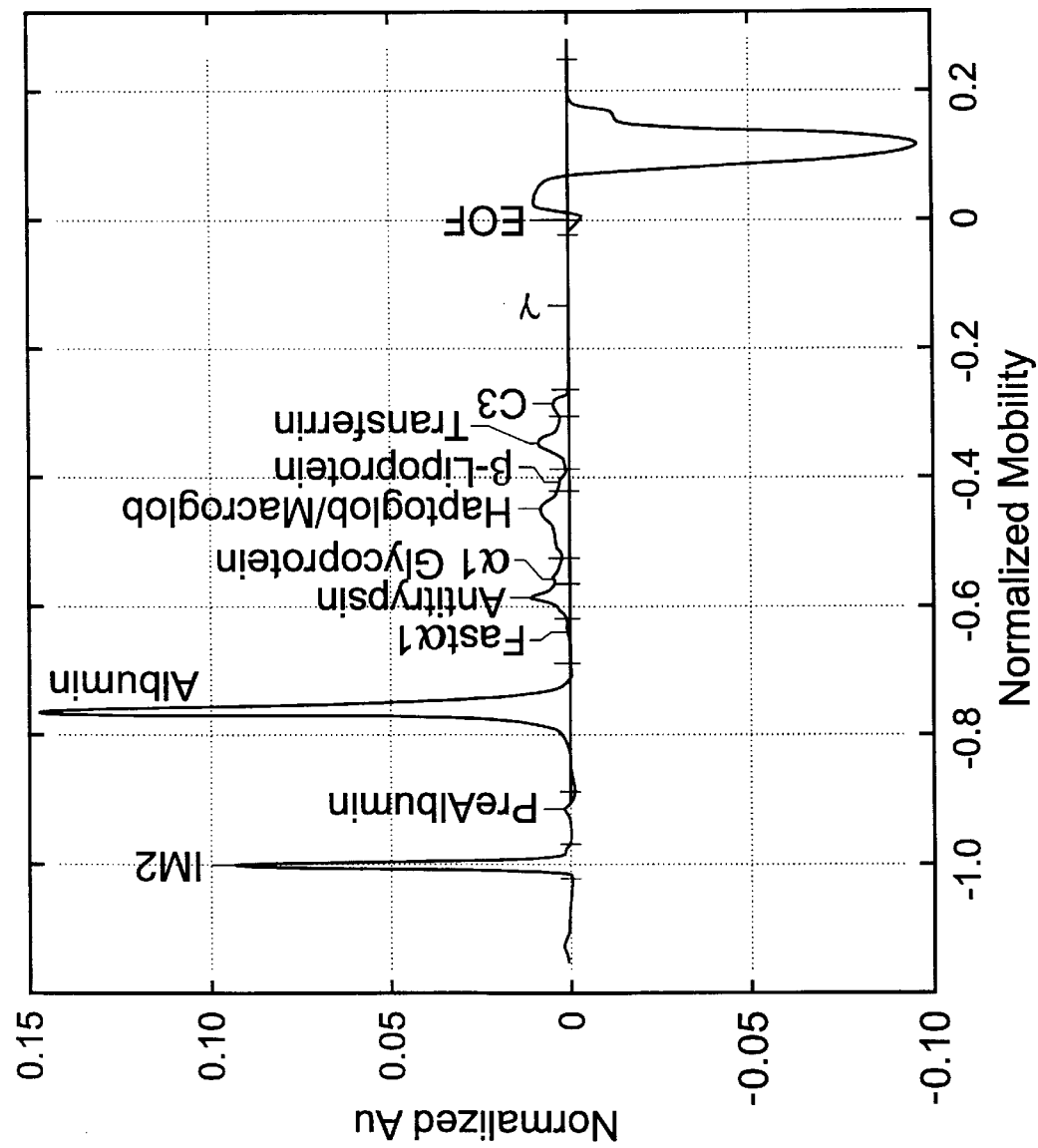
Figure 2C:
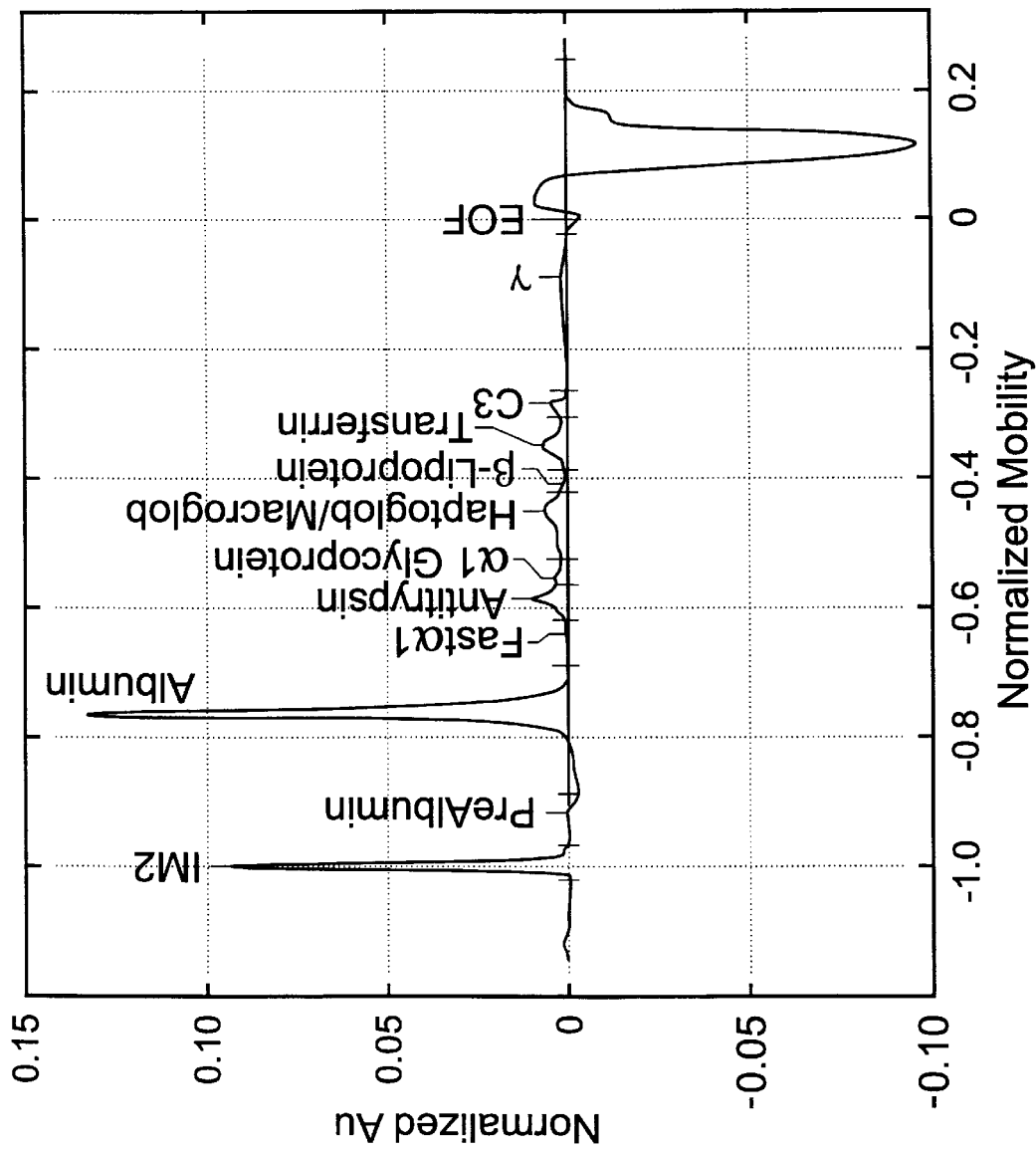
Figure 2D:
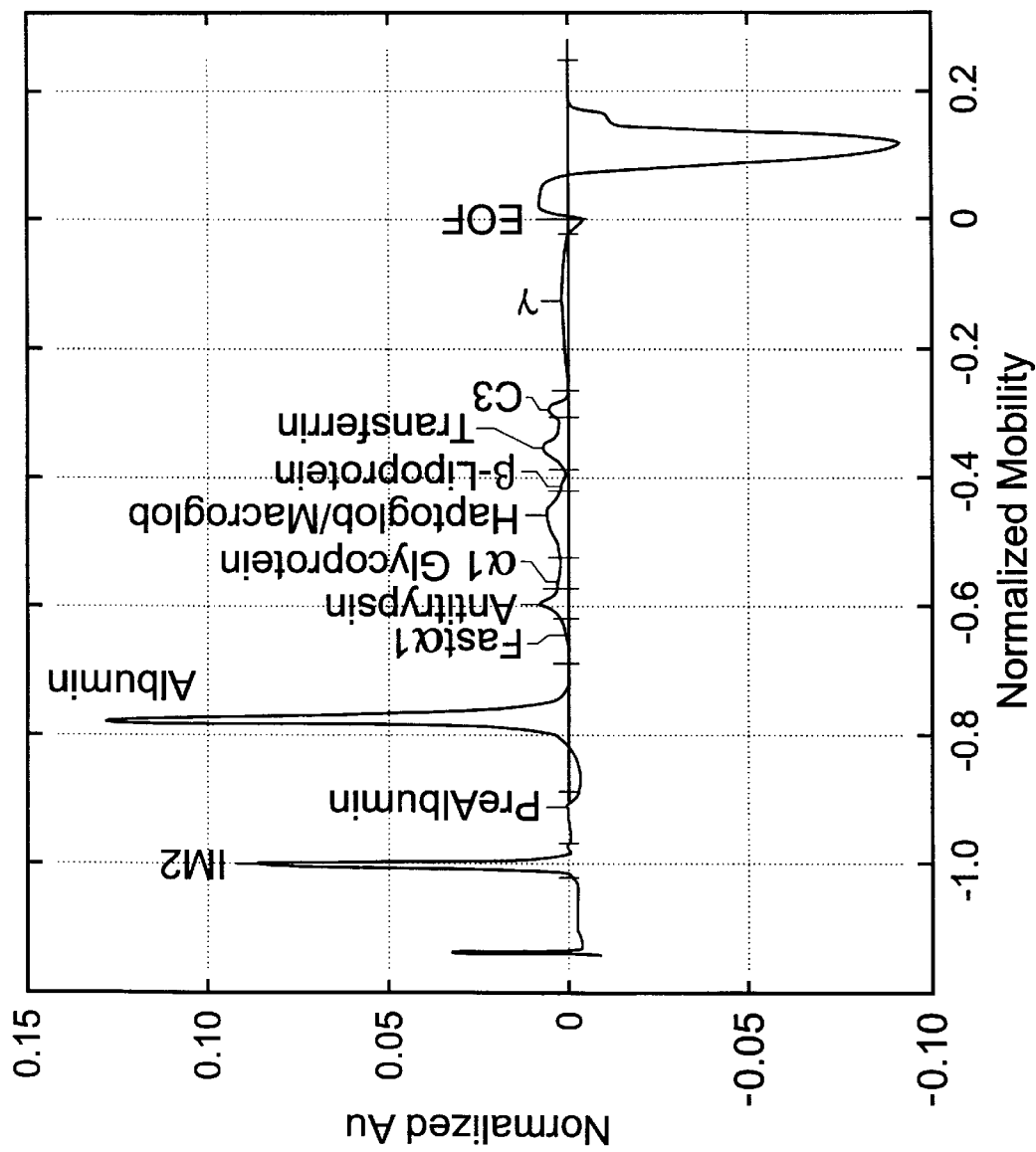
Figure 3A:
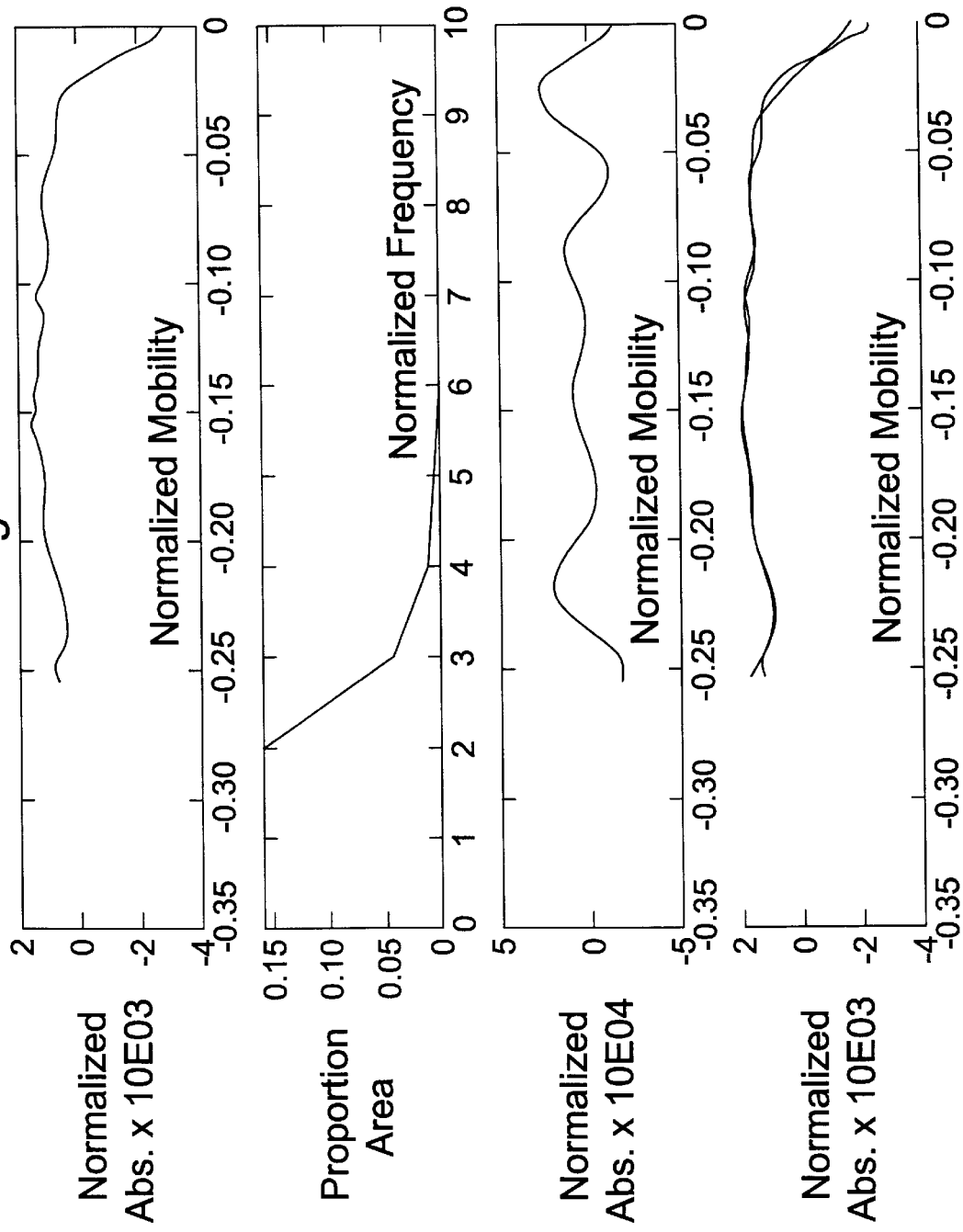
Figure 3C:
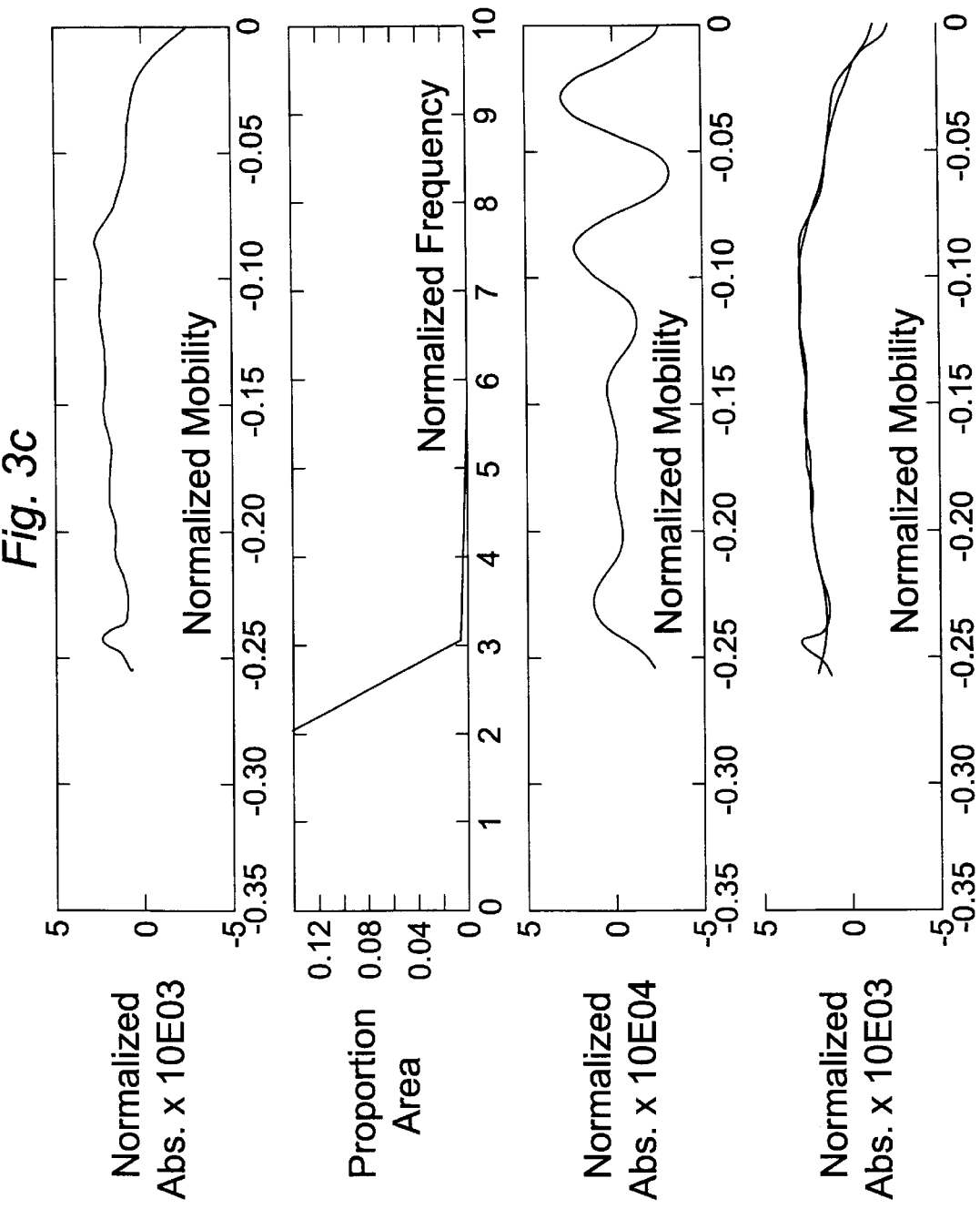

In one aspect, this invention relates to an automated immunosubtraction method of analyzing a biological sample for the presence or absence of at least one constituent of interest; the immunosubtraction method involves:

(a) mixing at least one aliquot of the biological sample with at least one specific binding partner that is capable of significantly removing at least one constituent of interest to generate a first treated sample;

(b) separating a portion of the first treated sample into constituent parts to generate a first data set; and (c) subjecting at least a portion of the first data set to a first analysis to generate a parameter set indicative of the at least one constituent of interest.

In an especially preferred embodiment, the method further includes:

(d) assigning a binary decision code to the first treated sample using the generated parameter set; and (e) comparing the binary decision code to a matrix of expected results to identify the constituent of interest.

In a preferred embodiment, the biological sample of the present invention is a serum sample. The constituents of interest are preferably paraproteins. The methods of the present invention can be used to identify the class and light chain type of paraproteins identified during serum protein electrophoresis screening.

Multiple myeloma is associated with an increase in serum protein levels of IgG, IgA, IgD, IgM or IgE as well as kappa- or lambda-light chains. The automated detection of such paraproteins is facilitated by the fact that paraprotein concentration levels are particularly amenable to capillary electrophoresis analysis. Elevated paraprotein concentration levels show a concomitant increase in signal. The signal produced by normal serum proteins leads to a smooth response. In contrast, the presence of a homogeneous component (a paraprotein) produces a locally sharper response in the normally smooth serum protein response.

In certain aspects, the method of the present invention uses differences in the frequency characteristics between biological samples which have been treated with specific binding partner(s) to identify the paraprotein. Biological samples which have not been treated with a specific binding partner, or samples that contain a different paraprotein than was specific for the binding partner added, are expected to contain more frequency components at the characteristic frequencies than smooth peaks. The smooth peaks are indicative of the paraprotein not initially being present or of the paraprotein being removed by the specific binding partner.

In a preferred embodiment of the present invention, a serum sample is separated into four aliquots, aliquots 1–4. Each aliquot is then treated with a specific binding partner or mixture thereof. The specific binding partners include, but are not limited to, anti-IgG, anti-IgA, anti-IgM, anti-IgD, anti-IgE, anti-kappa, anti-lambda, protein G or a mixture thereof. Preferably, the specific binding partners are covalently bound to beads and will significantly remove the component of interest from solution up to the binding capacity of the system. More than one specific binding partner can be added to a single aliquot. In another embodiment, the binding partner of interest will affect the mobility of the component of interest so as to allow discrimination of the bound component response from the free component response. The set of samples mixed with these combinations of specific binding partners form a sample panel. In a preferred embodiment, four aliquots are analyzed. In this embodiment, aliquot 1 is treated with a mixture of anti-IgG:anti-IgA; aliquot 2 is treated with a mixture of anti-IgG:anti-IgM; aliquot 3 is treated with anti-kappa; and aliquot 4 is treated with anti-lambda. The foregoing specific binding partners are known as the "standard set."

The specific binding partners, which in a preferred embodiment are specific binding proteins, are covalently attached to a solid support or added free in solution. If covalently attached to a solid support, the solid support is typically a gel, a bead or a microparticle. If a bead is used, it is preferably an agarose bead. The size or density of the beads is such that they do not enter the capillary and interfere with the capillary electrophoresis. In most instances, there is no need to remove the beads before the electrophoresis analysis.

The beads are thus used to significantly remove the constituent of interest. This procedure is an immunosubtraction procedure. As used herein, the term "immunosubtraction" describes a procedure wherein an immunoglobulin in a biological or serum sample will bind to an insolubilized antibody wherein the antibody is specific for the immunoglobulin. The immunoglobulin present in the serum is thus significantly removed from the serum or biological sample.

The term "significantly removed," as used herein, does not necessarily mean completely removed without a trace. In most instances, the antibody is covalently attached to a solid support which is insoluble in the biological sample. Thus, by adding the bound antibody to the sample, the specific immunoglobulin will bind to the antibody and thereby be pulled out of solution up to the capacity of the system.

For example, if the specific binding partner pair of anti-IgG:anti-IgM are admixed with a sample containing only the IgG immunoglobulin, the anti-IgG will bind to the IgG immunoglobulin and form an antibody-antigen conjugate. The IgG immunoglobulin will no longer be solubilized in the serum sample. The IgG immunoglobulin is thereby significantly removed from the biological sample.

Antibodies such as anti-IgG, anti-IgA, etc., are commercially available from Incstar of Stillwater, Minn., and are raised in goats against human immunoglobulins. The IgG of the goats is then purified from the serum. The antibodies are absorbed with the non-target immunoglobulins to remove cross reactivity.

The antibodies are coupled to beads, such as an agarose bead, in a ratio of about 10 mg to about 100 mg per mL of settled gel. More preferably, in a ratio of about 15 mg to about 30 mg per mL of settled gel. The gel is preferably an agarose based gel. Suitable gels include, but are not limited to, cross-linked p-nitrophenylchloroformate activated beaded agarose, etc. Coupling to the bead is done in a buffered solution and quenched with ethanolamine hydrochloride. The beads are then rinsed with buffer and diluted with deionized water.

Affinity purified or monoclonal antibodies can also be used with the methods of this invention. In addition, other specific binding partners, such a protein G or biotin, can be used.

The amount of specific heavy chain binding partner to paraprotein in the aliquot is about 1:1 to about 1:15, more preferably about 1:4 to about 1:10, and most preferably about 1:6. The amount of specific light chain binding partner to paraprotein in the aliquot is about 1:1 to about 1:15, more preferably about 1:6 to about 1:14, and most preferably about 1:12.

After the aliquot of the biological sample is mixed with a specific binding partner(s), it is then a "treated sample." As explained above, since a sample which contains a paraprotein has a higher proportion of characteristic components than a normal serum protein sample, examination of the characteristic frequency area, the proportion of the characteristic frequency area and the presence and magnitude of paraprotein features will specifically indicate a change in the paraprotein concentration of a treated sample.

After removal of the components of interest from the sample aliquots by the specific binding partner(s), the remaining components are separated by electrophoresis using methods well known to those skilled in the art. In an especially preferred embodiment, capillary electrophoresis is used for separation of each treated sample.

Capillary electrophoresis facilitates the analysis of small samples using high voltages and relatively short separation times. A preferred form of capillary electrophoresis, as used in the present invention, is "capillary zone electrophoresis," in which the separation medium is a buffer solution.

Conventional capillary electrophoresis units and materials are commercially available from suppliers such as Bio-Rad Laboratories (Hercules, Calif., USA). Operating conditions and procedures used for the separations are similarly conventional and can be selected and employed using methods known to those of skill in the art. A particularly preferred system for capillary electrophoresis is the Biofocus 2000 with CDM 2.0 software, available from Bio-Rad Laboratories.

The capillaries used for the biological samples, such as serum protein separation, will typically be capillaries of silica-containing material, preferably fused silica whose internal surface has not been coated. Other useful capillaries are glass or quartz. The internal diameters of the capillaries will typically be from about 20 $\mu$m to about 75 $\mu$m. Preferably, the capillaries used are those having internal diameters of about 25 $\mu$m to about 35 $\mu$m, more preferably about 25 $\mu$m. Capillaries of the type noted and preferred for serum protein electrophoresis can be obtained commercially from Bio-Rad. In other embodiments, the present invention will use electrophoretic separations performed in slab-shaped cells and other non-capillary systems.

Separations of biological or serum components will typically use conditions which are readily determined by those of skill in the art. Preferred conditions are described in U.S. Pat. No. 5,660,701, issued Aug. 26, 1997, which is incorporated herein by reference. The run buffer will typically be an aqueous solution of glycine with added acid or base. In one group of embodiments, a preferred run buffer is Bio-Rad part #194-5101. Typically, the treated serum samples are diluted into an aqueous buffer prior to injection into the capillary. The diluent can be the run buffer, or it can be a lower conductivity solution to provide a higher resolution through a process known as stacking. The diluent can also contain internal standard(s) for calibrating the y-axis, or markers for calibrating the x-axis. Hippuric acid or xanthine can be used as an internal standard, as a marker, or both.

According to the method of the present invention, each treated sample is independently introduced into the capillary, a voltage is then applied and each treated sample is separated into its various components. For capillary systems, separations will be carried out using voltages of about 1 kV to about 30 kV, preferably about 5 kV to about 15 kV. The components are resolved into bands, which migrate along the capillary and past the detector.

Detection of the bands of proteins can be achieved by any method that is known to be applicable to capillary electrophoresis. One type of detection is ultraviolet absorbance detection. Direct UV-absorbance detection can be achieved by passing a UV beam through the capillary, transverse to the capillary axis, and continuously monitoring the intensity of the beam emerging after having been interrupted by solute zones migrating across its path. The methods described herein are capable of detecting paraproteins at concentrations between 0.05 to 10 g/dL and as low as about 0.05–0.1 g/dL. This concentration is considered clinically significant, but can be easily missed by visual inspection of an electropherogram which has not been processed by the methods herein.

Detection of the component species from each treated sample provides a first data set. In some embodiments, the data can be used to plot an electropherogram. Alternatively, the first data set can be subjected to further analysis to generate an electropherogram capable of computer manipulation for area and peak height determination, normalization and zero correction.

After detection, the data from each treated sample is generally transferred to a digital processor (often a personal computer) as a series of digital amplitudes. The first amplitude is generally given an index number of zero or one. The index is generally incremented by one for each subsequent amplitude. For further analysis and/or presentation, the indices are converted to a more appropriate quantity with corresponding units, e.g., migration time in minutes.

A first data set obtained by the methods and of the type described above is preferably mobility zero corrected and normalized according to the methods discussed in co-pending application U.S. Ser. NO. 08/866,282, filed May 30, 1997, which is incorporated herein by reference.

For each treated sample, the frequency characteristics of a selected serum protein region or regions of interest is examined using Fourier analysis. The Fourier analysis will calculate the following parameters including, but not limited to, proportion of signal at frequencies typical of paraproteins, amount of signal at frequencies typical of paraproteins, presence or absence of a peak crest or shoulder at the suspect point and the amount of signal in the vicinity of the suspect point after applying a high frequency filter. The later parameter is known as the residual.

The signal of interest is interpolated to provide $2^N$ equally spaced data points, a fast Fourier transform of the data is taken, and the power spectrum is constructed by multiplying the forward transform of the signal by its complex conjugate. The amount and proportion of signal in the power spectrum occurring in a defined characteristic frequency range are calculated. This calculation can involve different weightings of values over different frequency regions. If the amount or proportion of the characteristic frequency signal exceeds a certain threshold, the possibility exists that a high-frequency component (i.e., paraprotein) is present.

If an amount of characteristic frequency signal above threshold is found, then an additional step is carried out to ascertain the location of the region(s) in the scan exhibiting the characteristic frequency response. The forward transformed data is separated into two parts: a characteristic frequency part, and a non-characteristic frequency part. For this application, the characteristic frequency part contains relatively high frequencies and thus may be thought of as the high frequency part, and the non-characteristic frequency part may be thought of as the low frequency part. Back-transforming the noncharacteristic (low) frequency part gives a "smoothed" data set which can be subtracted from the original (first) data set to provide a residual data set. Back-transforming the characteristic (high) frequency part provides the residual data set directly. Residual segments (another parameter) are defined and examined, and the maximum height of each residual segment is found. If the maximum positive deviation of the residual segment exceeds threshold, this location of maximum deviation is stored as a possible site of paraprotein. This step has two purposes. First, it eliminates some false positives found upon examination of the power spectrum alone. Second, this step gives an estimate of the location of possible characteristic frequency (i.e., paraprotein) features.

However, some false positives survive through both of these steps. For example, a sudden change in shape at the end of a delimited region, due to an improperly placed delimiter, can contribute characteristic frequency components to the power spectrum, and produce fairly large residuals at the ends of the delimited region under examination. To prevent these end segments from triggering false positives, a verification of the residual results is performed.

The verification of results found by Fourier analysis can be accomplished using a feature pick algorithm used in CDM 2.0 software (available from Bio-Rad Laboratories). A paraprotein response is expected to appear as either a crest or a shoulder. Thus, shoulders and crests found by the feature pick algorithm in the time domain are valid features of interest. This time domain information is also available in normalized mobility units. The location of the valid feature (s) found in the time domain is checked versus the location of the valid residual deviation(s) found through Fourier analysis. If a feature found by this independent check matches the location of a found residual segment maximum within a specified threshold (0.03 normalized mobility units, for example), a paraprotein is considered detected, and the x-location of the paraprotein is taken to be the location of the feature(s) found by the peak-pick algorithm.

Once the location of paraprotein features is found in the treated sample, the response can be quantified, using either manual delimiting of the area under the response, or by more automated means. In this manner, Fourier analysis is used both to ascertain the presence of a paraprotein in a sample, and provide a set of parameters indicative of the relative amount of paraprotein present in the sample.

Thus, in another aspect, the present invention provides a method to generate a set of parameters using a Fourier analysis of the data set obtained from the separation step. This Fourier analysis or "check analysis" comprises:

(i) subjecting at least a portion of the first data set to Fourier transform to generate forward-transformed data sets;

(ii) finding the proportion area of the characteristic frequency region, and the area of the characteristic frequency region;

(iii) selecting any forward-transformed data set having a characteristic frequency component above a first preselected threshold;

(iv) filtering and back-transforming data sets selected in step (iii) to provide filtered, back-transformed data sets;

(v) identifying the magnitude and location of residual maxima in the filtered, back-transformed data sets;

(vi) comparing the location of any residual maxima having a magnitude above a second preselected threshold to a corresponding location in the first data set; and (vii) finding the position and magnitude of any found feature(s) to detect the presence of paraproteins in a biological sample and forming a parameter set indicative of the paraproteins of interest.

Although Fourier analysis (including Fourier transformation of the data) is the preferred analysis method of the present invention, other mathematically equivalent methods can be used to provide a forward-transformed data set. Fourier transformation is a well-known mathematical process for the conversion of time or position data into frequency data. All of the first data set can be transformed at this point, or just that portion which represents a paraprotein region. In a delimited data set, the limits are typically set at about 0 to about −0.4 and, more preferably, at about 0 to about −0.3. The delimited portion will typically correspond to the gamma region, but could also correspond to other regions including, but not limited to, the beta, C-3, transferrin, alpha 2, or alpha 1 regions. The forward-transformed data set thus generated can be used to construct a power spectrum for visual examination.

To determine whether the distribution of the power spectrum response over frequency indicates the presence of a paraprotein, a characteristic frequency region is defined. The boundaries between the characteristic frequency region and any low and high frequency regions surrounding it, can be defined as abrupt or gradual transitions. It has been found that a linear transition is both convenient and suitable. Because of noise and spikes, detection is improved by limiting the extent of the high frequency region examined. If the high frequencies have already been excluded by prior filtering, the results are not sensitive to the upper boundary. By altering the transition points, all high frequencies can be examined, or, alternatively, a smaller subset. Typically, the lower frequency boundary of the characteristic frequency region occurs from about 0.005 to about 0.009 normalized frequency units, and the high frequency boundary of the characteristic frequency region occurs at approximately 0.009 to 0.012 normalized frequency units. Those data regions containing characteristic frequency components above the preselected threshold are selected and labeled as possibly abnormal regions. The preselected area threshold will typically be set at about $1\times10^{-4}$ to about $1\times10^{-2}$, and more preferably at about $9\times10^{-4}$. The thresholds are typically set to levels corresponding to concentrations of about 0.05 to about 0.1 g/dL. The preselected area threshold and frequency settings can be varied with the region examined. More than one frequency region and/or normalized mobility region may be examined and results from multiple regions queried using Boolian logic (e.g., "ANDed or ORed").

The forward transform data set is next filtered and back-transformed. Back-transformation is the reverse operation of Fourier transform. For example, if Fourier transforms are used to convert data from the time domain to the frequency domain, then a back-transform will convert the data from the frequency domain back into time. If the data has not been filtered, the back-transform will restore the original data set.

Filtering emphasizes those frequency components of interest. The forward transformed data is multiplied by a function designed to keep those characteristic frequencies of interest, and de-emphasize those non-characteristic frequencies not of interest. The set of characteristic frequencies may consist of a high frequency region, or any set of selected frequencies found to be indicative of the presence of paraproteins. The non-characteristic frequencies are those frequencies not used as characteristic of the presence of a paraprotein. The transition between a non-characteristic frequency region and a characteristic frequency region may be gradual or abrupt. Commonly, filtering is used to separate the data into a non-characteristic frequency region and a characteristic frequency region. Filters using a linear ramp in the transition region are convenient and suitable for this purpose. Filters typically used include low pass filters, high pass filters, bandpass filters, notch filters, or combinations thereof. Preferably, the filters used are high, low, and bandpass filters. In some embodiments, the filter used is a ramp smoothing filter. In other embodiments, a square smoothing filter is used.

If a filter is applied and the data set is then back-transformed, the back-transformed data will no longer match exactly the original data set. If a low pass filter has been applied, the back-transformed data set will be smoothed. If a characteristic frequency (high or bandpass) filter has been applied, the back-transformed data set will be a residuals data set. This is the residual parameter. The same residuals data set can also be constructed by subtraction of a data set filtered using the non-characteristic frequency filter from the first (original) data set.

The Fourier transforms and filtering functions can be done using the appropriate software. One example of such software is the MatLab routine named FFT from the MatLab programming environment (Math Works, Inc., Natick, Mass., USA).

The filtered, back-transformed data set can then be examined for the presence (magnitude and location) of residual maxima. These residual maxima correspond to potential paraprotein sites. Any residual parameters or residual maxima having a magnitude above a pre-selected threshold is considered to be the potential site of a paraprotein. The amplitude threshold is typically set at about $1\times10^{-5}$ to about $1\times10^{-2}$ normalized AU, and more preferably at about $2\times10^{-4}$ normalized AU. The amplitude threshold is typically set to levels corresponding to concentrations of about 0.05 to about 0.1 g/dL.

The data from each treated sample can be analyzed under various filter conditions, and if paraproteins are found using specified filtering conditions, the area can be identified as a paraprotein region. To verify the assignment, the results of an independent feature-pick routine are used to confirm that a feature exists in the predicted location. An example of this independent feature pick routine is the peak detection algorithm in CDM 2.0 software, available from Bio-Rad Laboratories, which selects valid shoulders and crests in the time domain. This time domain information is also available in normalized mobility units. The location of these features found in the time domain is checked versus the location of the valid residual deviation(s) found through Fourier analysis. If a feature found by this independent check matches the location of a found residual segment maximum within a specified threshold (0.03 normalized mobility units, for example), a paraprotein is considered detected, and the x-location of the paraprotein is taken to be the location of the feature(s) found by the peak-pick algorithm.

In this manner, the parameter set is generated through a combination of power spectrum characteristic frequency region examination, construction and examination of residual maxima, and verification using an independent feature-pick routine.

In certain aspects, the method of this invention further includes assigning a binary decision code (either negative or positive, i.e., 0 or 1) to each treated sample using the generated parameter set from the Fourier transformation. The generated parameter set includes, but is not limited to, proportion of signal at frequencies typical of paraproteins, amount of signal at frequencies typical of paraproteins, presence or absence of a peak crest or shoulder at the suspect point, magnitude of the response of the feature at the suspect point, and the amount of signal at the suspect point after applying a characteristic frequency filter (the residual).

Once these parameters have been generated, each treated sample is classified as either negative or positive by the evaluation of the parameters using a given set of criteria. To assign or classify the treated sample as positive or negative, the criteria which can be used include, but are not limited to, the following:

1) If no parameters are generated from the check analysis, the treatment is assigned a binary decision code which is negative.

2) If the parameter of "proportion of signal at frequencies typical of paraproteins" is below threshold, the treatment is assigned a binary decision code which is negative. The threshold can be set as a function of the highest and lowest proportion of signal among the four treatments in the standard set.

3) If the parameter of "amount of signal at frequencies typical of paraproteins" is below threshold, the treatment is assigned a binary decision code which is negative. The threshold can be set as a function of the highest and lowest amount of signal among the treated samples of the standard set.

4) If the parameter of "magnitude at the reference point" is less than threshold, the treatment is assigned a binary decision code which is negative.

5) In all other situations, the treatment is assigned a binary decision code which is positive, if at least one sample has sufficient subtraction to render a valid assay result. Otherwise, the sample result is ambiguous and no decision is made.

It is important to note that a negative assignment does not necessarily imply that the paraprotein was not present in the original biological sample or that the paraprotein is absent in the treated sample, only that the concentration of the paraprotein(s) is reduced.

After each treated sample is assigned a binary decision code, the results can be compared to a matrix of expected results. In an especially preferred embodiment, the serum sample has been treated with the standard set of specific binding partner(s) and a parameter set is generated for each treated sample. A binary decision code is assigned to each treated sample in the panel. The panel set is then compared to the standard set matrix of expected results to identify the constituent of interest. In this embodiment, the binary decision codes from four treated samples are examined simultaneously to deduce the class and light chain type of the paraprotein.

Table 1 is an example of a standard set matrix of expected results of the present invention.

TABLE 1

Treatments

| 1: Anti-IgG, Anti-IgA | 2: Anti-IgG, Anti-IgM | 3: Anti-Kappa | 4: Anti-Lambda | Results Class/Message |
|---|---|---|---|---|
| Negative | Negative | Negative | Positive | IgG, Kappa |
| Negative | Negative | Positive | Negative | IgG, Lambda |
| Negative | Positive | Negative | Positive | IgA, Kappa |
| Negative | Positive | Positive | Negative | IgA, Lambda |
| Positive | Negative | Negative | Positive | IgM, Kappa |
| Positive | Negative | Positive | Negative | IgM, Lambda |
| Positive | Positive | Negative | Positive | Kappa light chain, or possible IgE or IgD paraprotein |
| Positive | Positive | Positive | Negative | Lambda light chain, or possible IgE or IgD paraprotein |
| Negative | Negative | Positive | Positive | Free G heavy chain |
| Negative | Positive | Positive | Positive | Free A heavy chain |
| Positive | Negative | Positive | Positive | Free M heavy chain |
| Positive | Positive | Positive | Positive | No immunosorption has taken place. The feature may not be a paraprotein. |
| All Others | | | | The pattern does not match any known immunoglobulins |

The header of the table lists the standard set sample treatments, followed by a column for the assignment given for this combination of treatment results. This standard set of sample treatments consists of four treatments. As shown in the table, treatment 1 is a combination of anti-IgG and anti-IgA antibodies, treatment 2 is a combination of anti-IgG and anti-IgM antibodies, treatment 3 is anti-kappa antibody, and treatment 4 is anti-lambda antibody. The body of the table then lists the assignment given for each possible set of standard set treatment results. This set of result assignments is the matrix of expected results.

As explained above, after each treated sample is assigned a binary decision code, the results can be compared to a matrix of expected results. For instance, if the standard panel is used, i.e., aliquot 1 is treated with a mixture of anti-IgG:anti-IgA; aliquot 2 is treated with a mixture of anti-IgG:anti-IgM; aliquot 3 is treated with anti-kappa; and aliquot 4 is treated with anti-lambda and the assigned binary decision codes are negative, positive, positive and negative, the results indicate IgA, lambda (see, row 4).

The matrix of expected results illustrated in Table 1 allows for the identification of various paraproteins, and is specifically designed to identify paraproteins when the standard specific binding partner panel is used. It is possible to create various panels and matrices of expected results to identify paraproteins. The foregoing standard panel and matrix of expected results is illustrative and not limiting.

In another aspect, the present invention provides a method of monitoring paraprotein production in an individual, the method comprising:

(a) subjecting a first serum sample of an individual to capillary electrophoresis and detecting paraproteins at a first level using the method described above;

(b) subjecting a second serum sample of said individual to capillary electrophoresis and detecting paraproteins at a second level using the methods described above; and (c) comparing the first level and the second level to monitor the level of paraprotein production in the individual.

In this aspect of the invention, the comparing can be carried out by a skilled clinician or by computer programs which provide comparison routines, and the calculation of areas from a specific region, such as, for example, CDM 2.0 software available from Bio-Rad Laboratories.

The following examples are offered for purposes of illustration only.

EXAMPLES

To illustrate the analysis method, three examples are provided.

Example 1

This example illustrates a response when the concentration of paraprotein is limited.

In the case of a small paraprotein response superposed on a normal response, the bead-coupled anti-antibody is expected to bind to virtually all of the component(s) in solution capable of binding to the beads, thus significantly removing these components from solution. Thus, the feature associated with the paraprotein is not expected to appear in the samples which bind to the anti-antibody. If only one abnormal protein type is present in the sample, a large difference in the proportion high frequency area is expected with the treatments where the paraprotein is effectively removed, leaving a relatively broad unbound normal response remaining. The absolute area in the high frequency area region is also expected to decrease.

This first limiting case is illustrated using FIGS. 1–4. The untreated sample is shown in FIG. 1. The IgG, lambda paraprotein is located in the gamma region at normalized mobility −0.093. FIGS. 2A–D show a first data set from a panel of treated samples which is inputted into the paraprotein analysis method. FIG. 2A shows the sample response obtained after treatment with panel item 1—beads containing a mixture of anti-IgG:anti-IgA immunoglobulins. This treatment is expected to reduce or remove the paraprotein, due to the presence of the IgG antibody along with a large proportion of the "normal" response, and inspection of the plot shows that this is the case. FIG. 2B is the sample response obtained after treatment with panel item 2—beads containing a mixture of anti-IgG:anti-IgM immunoglobulins. This treatment is also expected to reduce or remove the paraprotein along with a large proportion of the "normal" response, due to the presence of the anti-IgG. Inspection of the FIG. 2B shows that this is the case. FIG. 2C is the sample response obtained after treatment with panel item 3—beads containing anti-kappa. This treatment is not expected to subtract the paraprotein, but is expected to subtract a large amount of the "normal" response. FIG. 2D is the sample response obtained after treatment with beads containing anti-lambda. This treatment is expected to subtract the paraprotein, and inspection shows that this is the case.

FIGS. 3A–D are a set of four graphs which provide an illustration of the Fourier Analysis results from each of the individual sample treatments. The top subplot in FIGS. 3A–D shows the determination of paraprotein features for each panel sample. A paraprotein feature was found in FIG. 3C in the vicinity of −0.093 normalized mobility units, with no suspect paraprotein features being found in the other panel items. The lower three subplots illustrate the method used to make the paraprotein feature determination using the method in U.S. Ser. No. 08/895,247. The second subplot in FIGS. 3A–D shows the power spectrum generated for each panel item, with proportion area specifically being plotted in this instance. If the proportion area found in the power spectrum exceeds threshold, the presence of paraproteins in the specified region is further considered. The third subplot in FIGS. 3A–D represents the back-transform of the data in the first subplot after it has been filtered to exclude the non-characteristic frequency part. These residuals are used to determine the possible position of paraprotein components if the high frequency characteristics of the signal indicate that paraprotein(s) may be present. These possible paraprotein locations are then verified using an independent peak-pick method before a paraprotein feature is indicated as a result. The fourth subplot in FIGS. 3A–D is a comparison between the original data and a back-transform of the non-characteristic frequency part of the data.

FIG. 4 is the result obtained by running this sample panel through the method of the present invention. The correct location of the feature was input to the algorithm, as well as a spurious location. The method correctly identified the identity of the component at −0.0930 normalized mobility units, IgG, lambda, and also correctly gave the result that it could not identify the component at the normalized mobility of −0.1210 normalized mobility units. Feature 1 Analysis: treatments 1, 2, and 4 yield check region results of negative (−), with no paraproteins found. Therefore, these samples are assigned the result low (−). Treatment 3 yields a check region result of positive, and one valid feature is found by the check region algorithm at −0.0893 normalized mobility units, giving a high (+) result for this sample. This set of panel results [−,−,−,+,−] yields the correct result for Feature 1: IgG, Lambda. Feature 2 Analysis: no features passing the check region criteria are found in the vicinity of −0.1210 normalized mobility units, yielding a low (0) result for all sample treatments. This set of panel results [−,−,−,−] yield the correct result for Feature 2: NO ASSIGNMENT.

Example 2

This example illustrates that when a large paraprotein response was superposed on a normal response, the amount of binding pair (antibody) coupled to the beads is insufficient to totally remove the abnormal component.

Due to the fact that the abnormal component will dominate the region, even in the panel samples where the maximum possible amount of paraprotein is subtracted out, the proportion in the characteristic frequency area may remain essentially constant, but the absolute area in the high frequency area region is expected to decrease in those samples in which the paraprotein is removed.

FIG. 5 is a graph which shows a serum protein sample with a large paraprotein result in the gamma region, at a normalized mobility of approximately −0.16. The paraprotein at normalized mobility of −0.16 is known to be of type IgM, kappa.

Figure 6A:
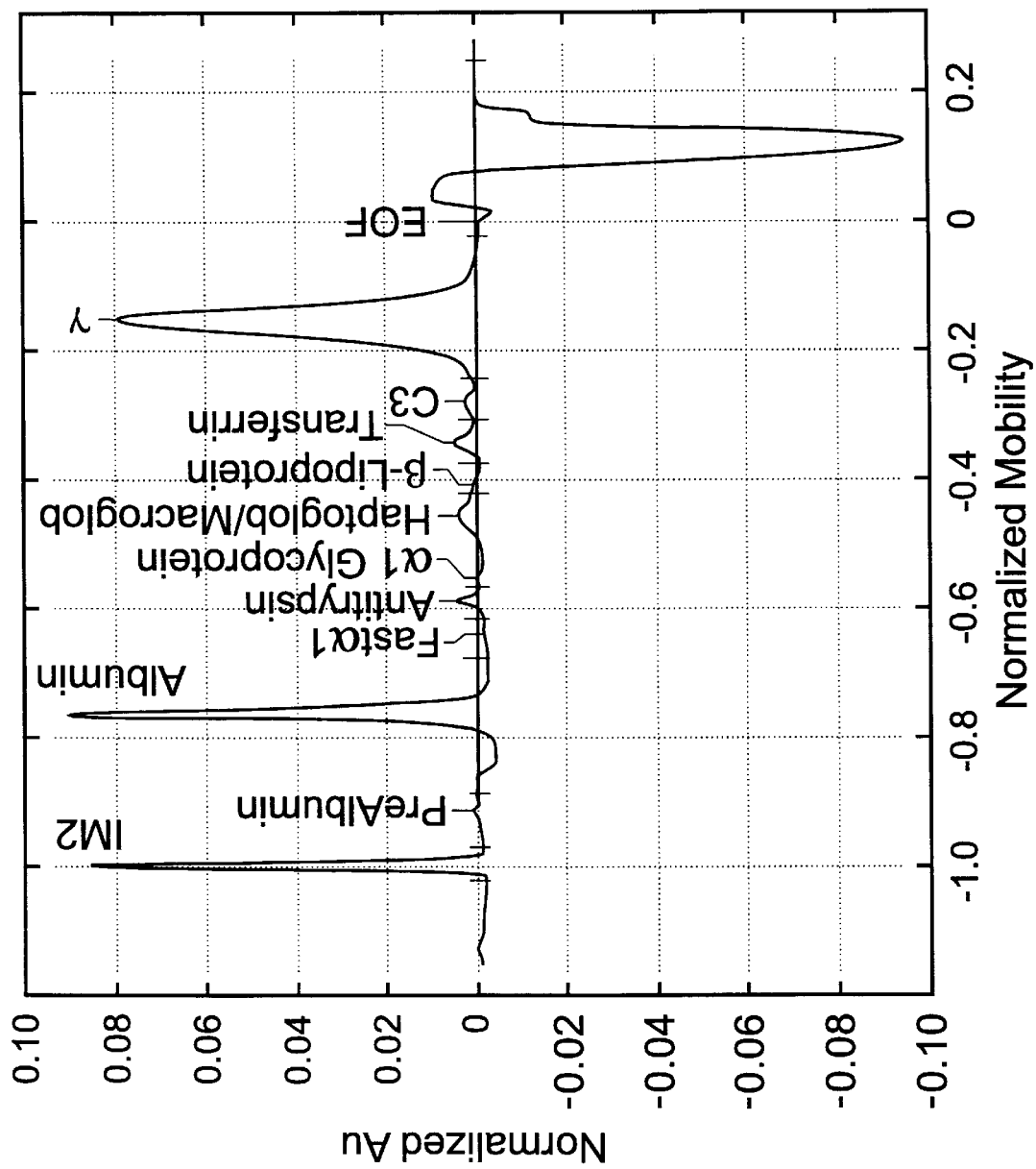
Figure 6B:
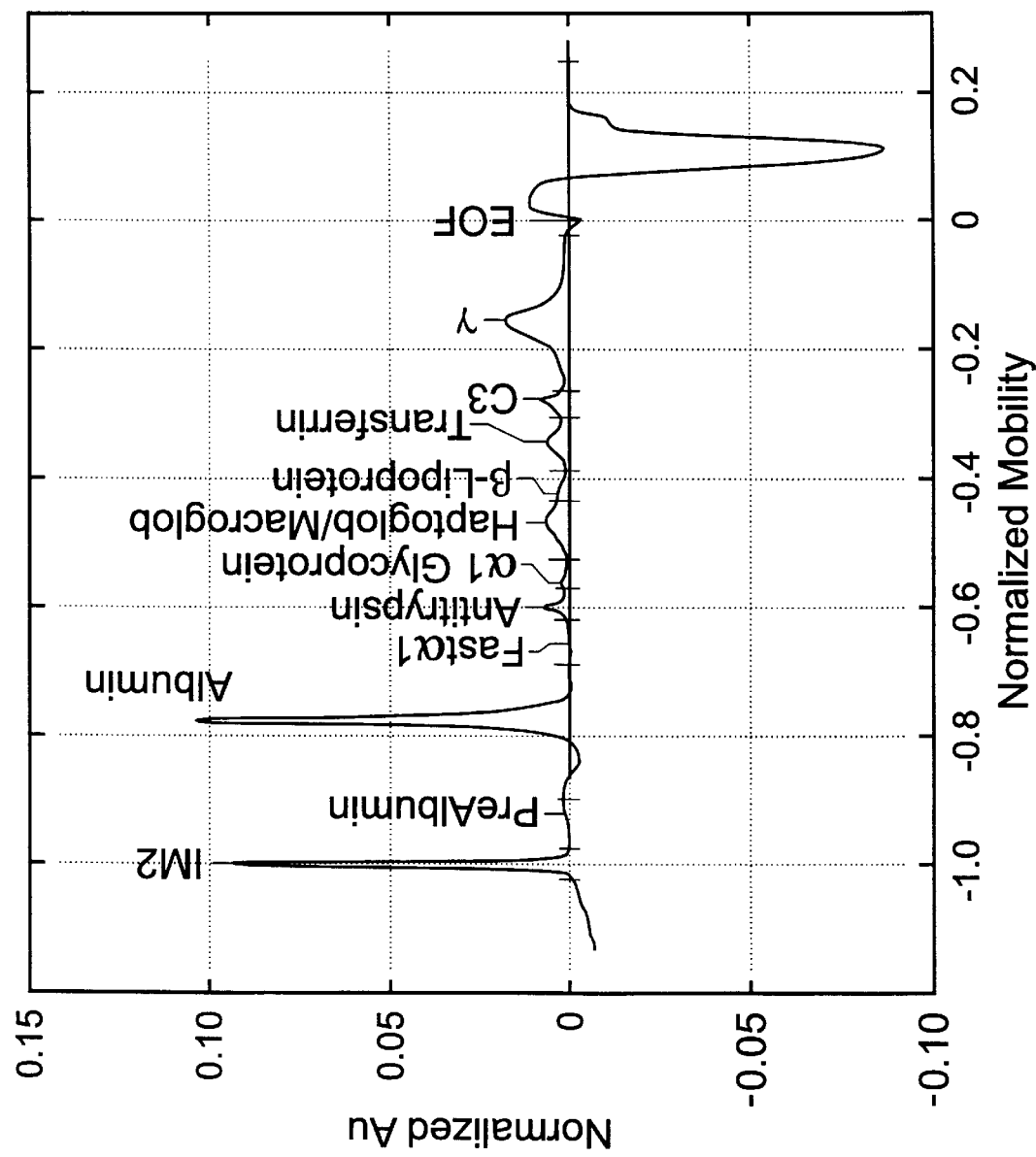
Figure 6D:
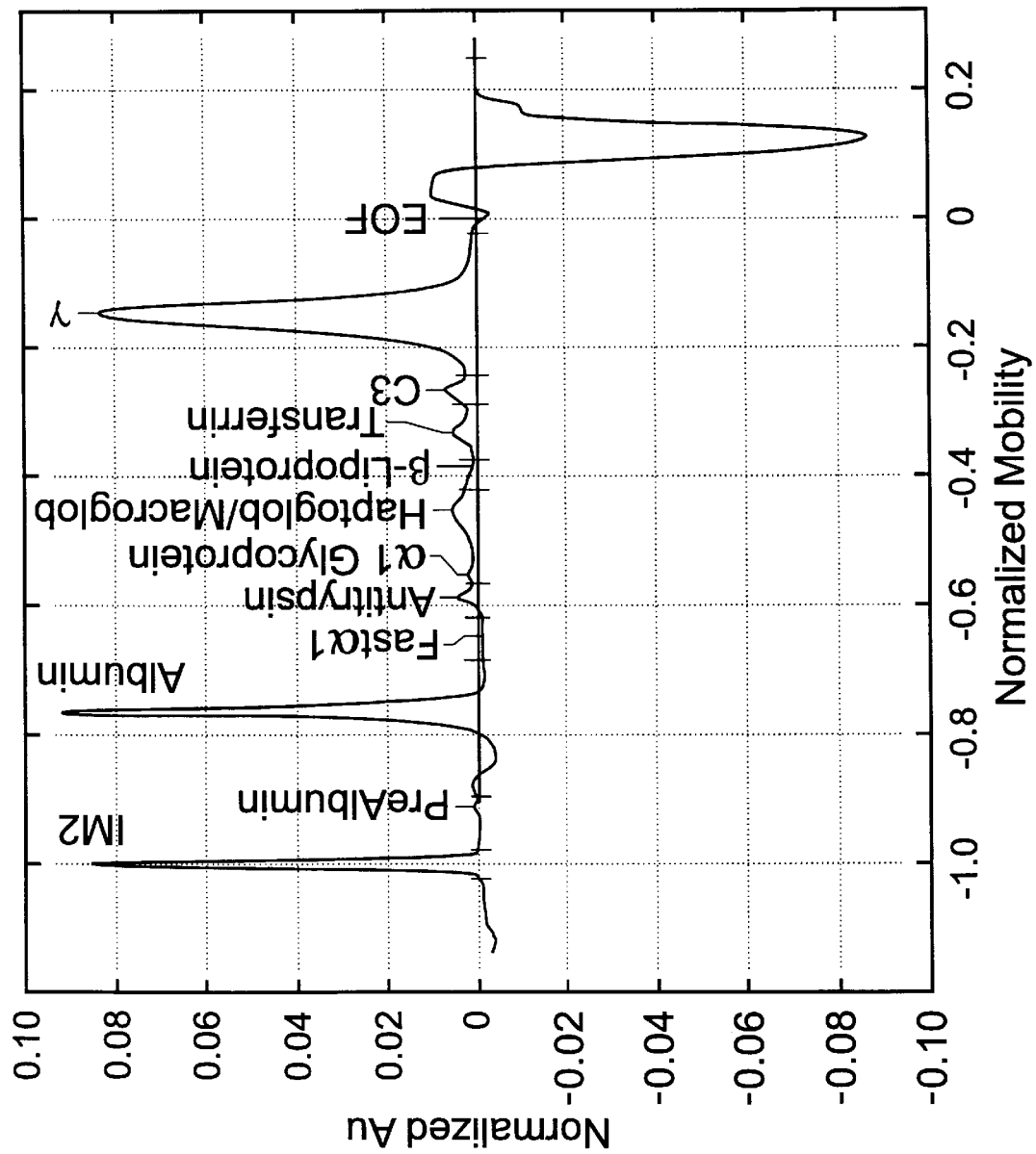
Figure 7C:
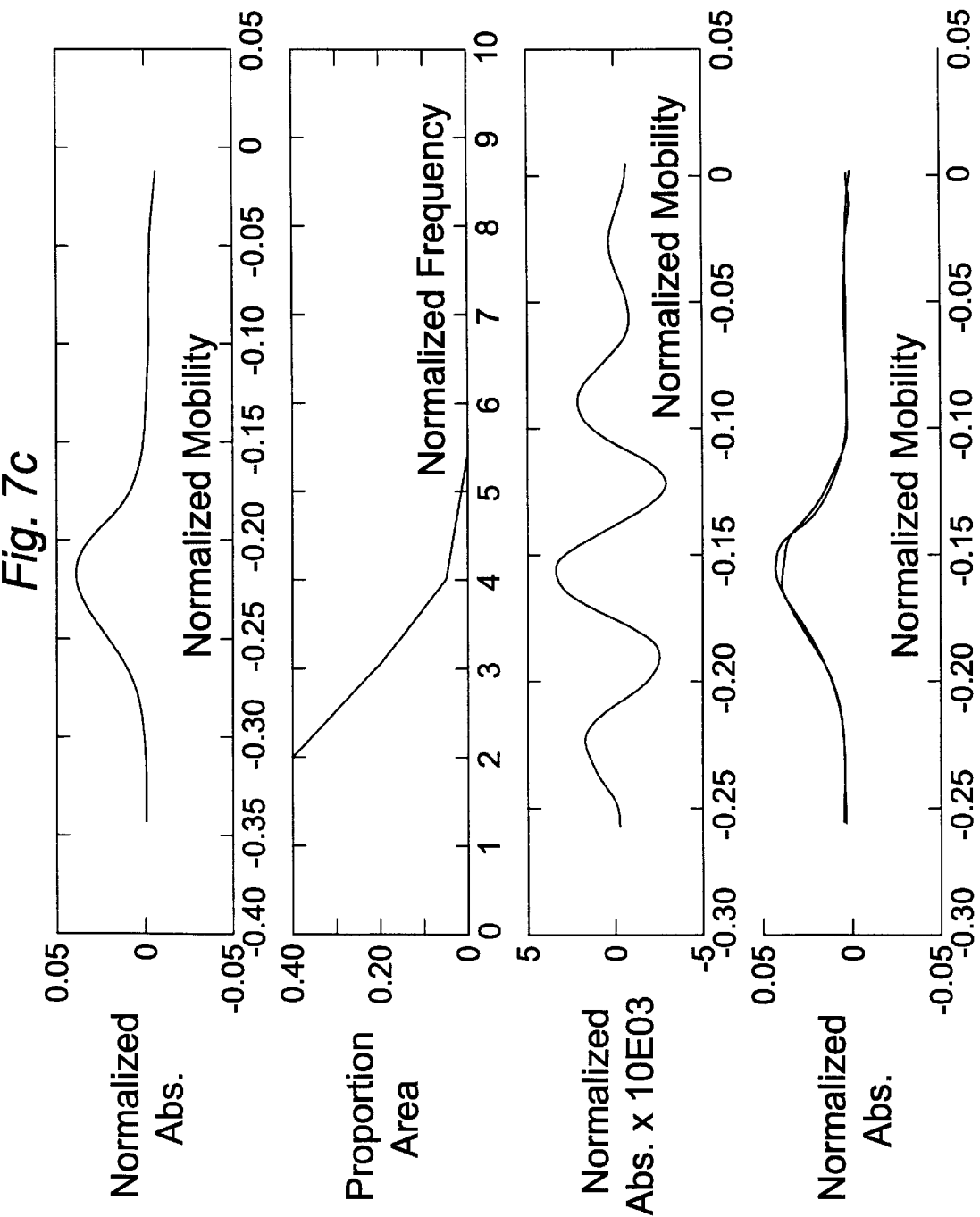
Figure 7D:
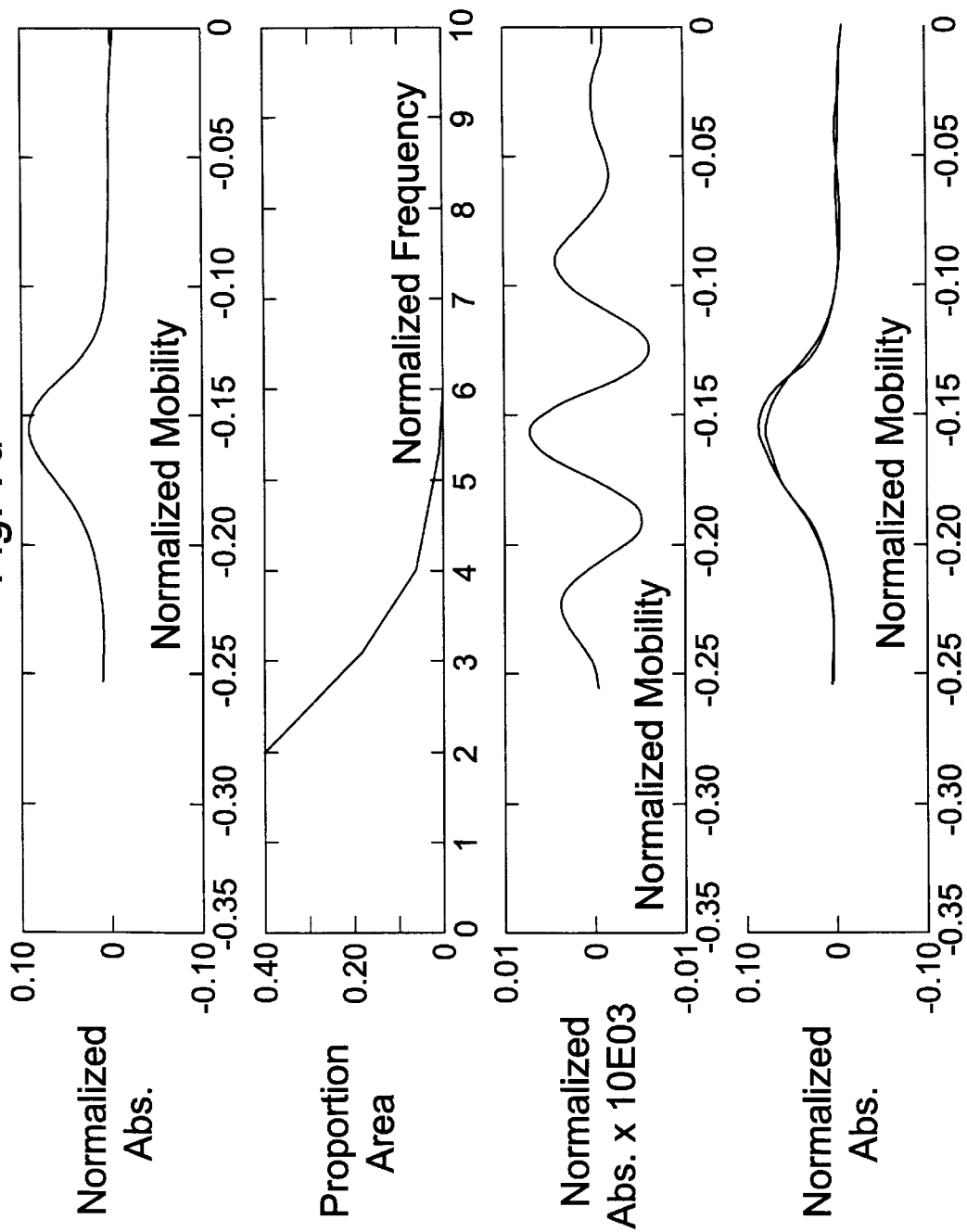

FIGS. 6A–D are a set of four graphs showing a first data set of a panel of treated samples containing a large paraprotein. FIG. 6A is a sample response obtained after treatment with beads containing anti-IgG:anti-IgA immunoglobulins. This treatment is not expected to reduce or remove the paraprotein, and inspection of the plot shows that this is the case. FIG. 6B is a sample response obtained after treatment with beads containing anti-IgG:anti-IgM immunoglobulins. This treatment significantly reduces the paraprotein, due to the presence of the IgM antibody, but does not completely remove it. FIG. 6C is a sample response obtained after treatment with beads containing anti-kappa light chain. This treatment significantly subtracts the paraprotein, but does not totally remove it. FIG. 6D is a sample response obtained after treatment with beads containing anti-lambda light chain. This treatment does not significantly subtract the paraprotein.

FIGS. 7A–D are a set of four graphs which provide an illustration of the Fourier Analysis results from each of the individual sample treatments. The top subplot in FIGS. 7A–D shows the final result of the analysis. The feature of interest is found in all samples. The second subplot in FIGS. 7A–D shows the power spectrum generated, with proportion area specifically being plotted in this instance. The third subplot in FIGS. 7A–D represents the back-transform of the data in the first subplot after it has been filtered to exclude the non-characteristic frequency part. The fourth subplot in FIGS. 7A–D is a comparison between the original data and a back-transform of the non-characteristic frequency part of the data.

FIG. 8 is the result obtained by running this sample panel through the method of the present invention. The correct location of the feature was input to the algorithm. The method correctly identified the identity of the component at −0.16 normalized mobility units as IgM, kappa. Feature 1 Analysis: all treatments yield check region results of positive (+), and a valid feature is found in the vicinity of −0.1600 normalized mobility units for each sample treatment. Treatments 2 and 3 give absolute characteristic area values below threshold, while treatments 1 and 4 give absolute characteristic area values above threshold. Thus, treatments 2 and 3 are assigned the value low (−), and treatments 1 and 4 are assigned the value high (+). This set of panel results [+,−,−,+] yield the correct result for Feature 1: IgM, Kappa.

Example 3

This example illustrates the situation when two paraproteins exist in a single region, one of type IgG, kappa, and the other of type IgG, lambda.

The two locations are far enough separated from each other so that they can be considered separately. The two specified locations are considered separately by the algorithm, and identifications made for both.

Figure 9:
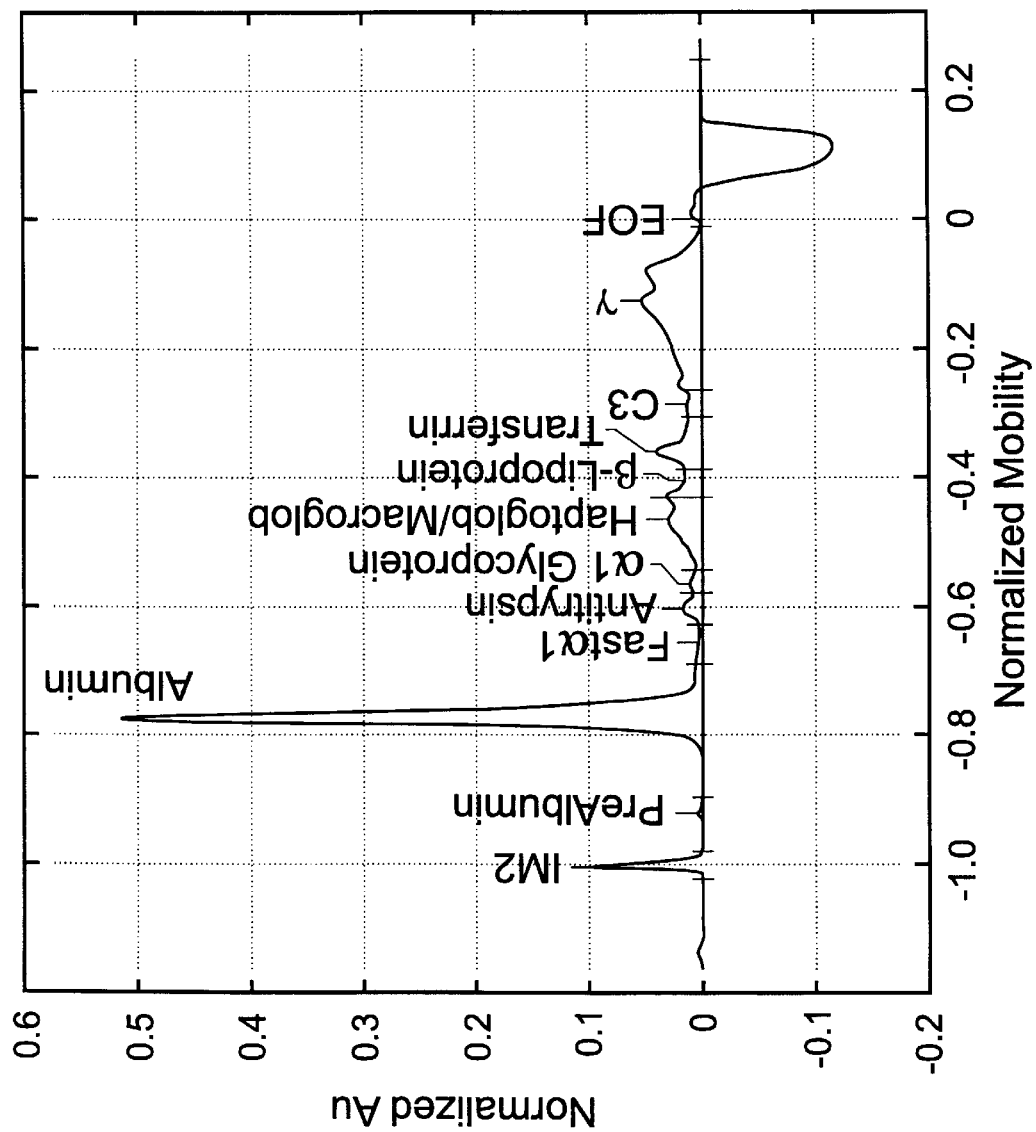
FIG. 9 is a graph which shows a serum protein sample with two small paraproteins present. The first paraprotein, with a normalized mobility of −0.07, is known to be of type IgG, kappa, and the second paraprotein, with a normalized mobility of −0.12, is known to be of type IgG, lambda.

FIG. 9 is a graph which shows a serum protein sample with two small paraproteins present. The first paraprotein, with a normalized mobility of −0.07, is known to be of type IgG, kappa, and the second paraprotein, with a normalized mobility of −0.12, is known to be of type IgG, lambda.

Figure 10A:
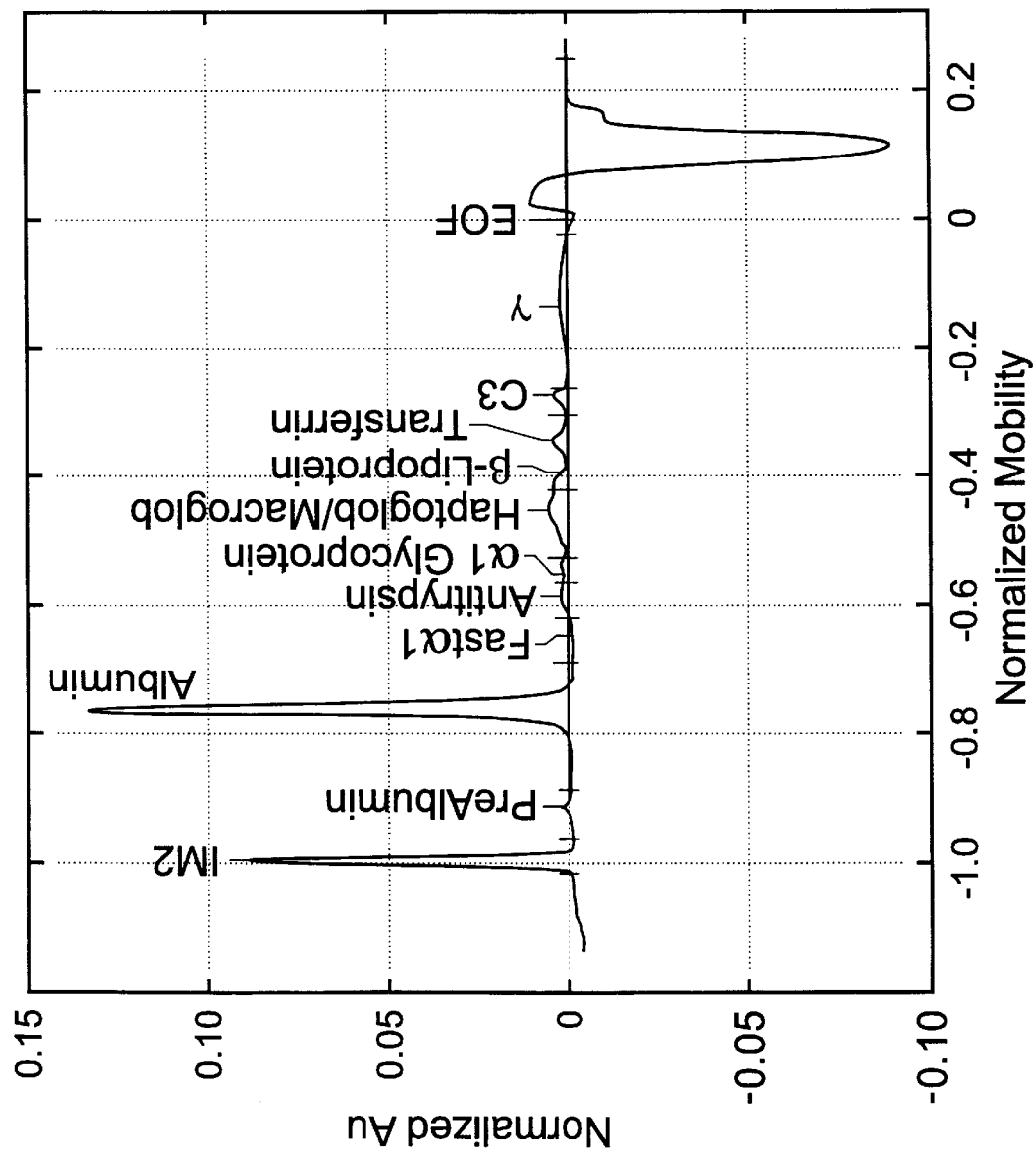
Figure 10B:
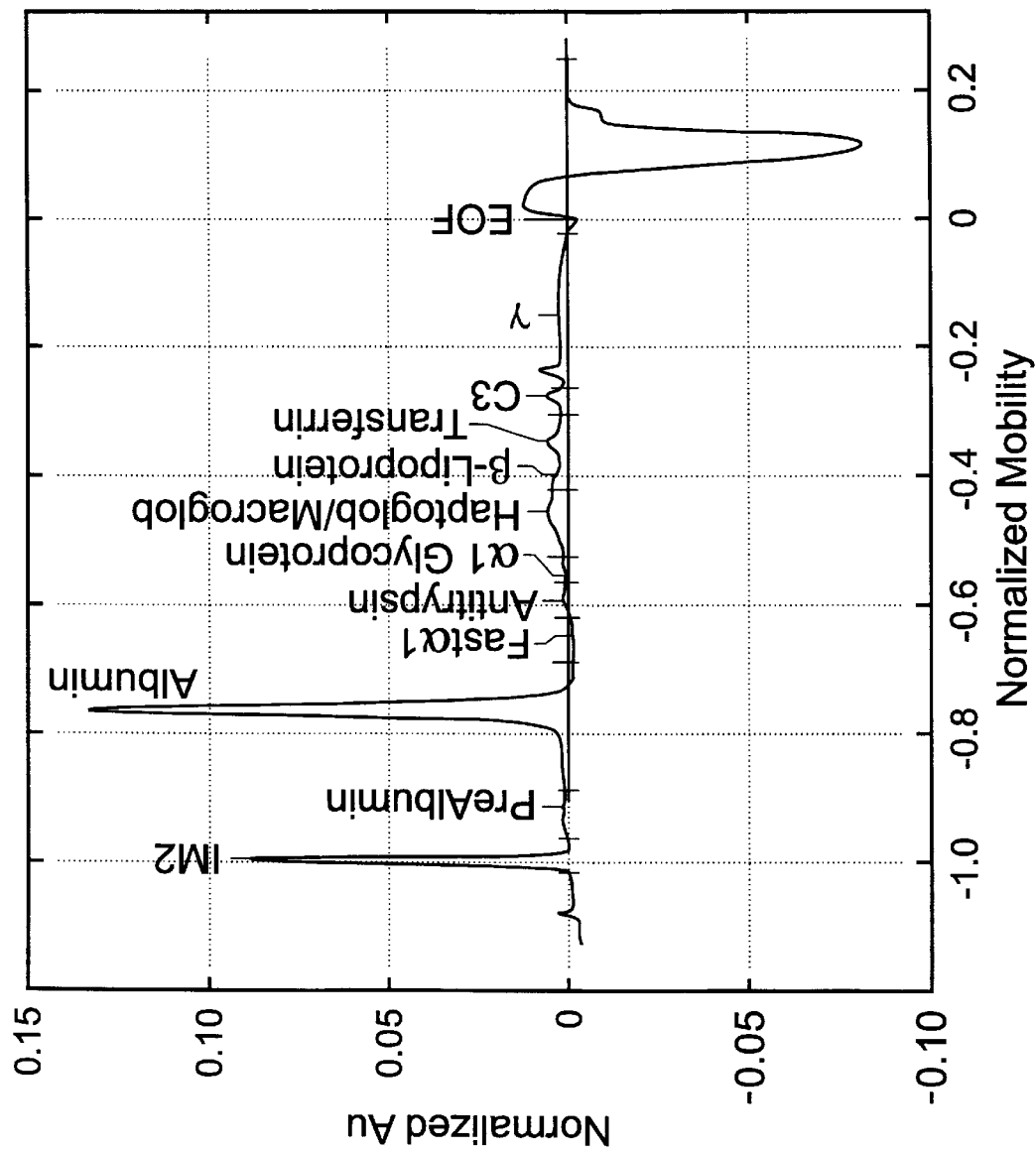

FIGS. 10A–D are a set of four graphs showing a first data set of a panel of treated samples containing two paraproteins of differing type. FIG. 10A is a sample response obtained after treatment with beads containing a mixture of anti-IgG:anti-IgA immunoglobulins. This treatment is expected to remove both paraproteins, and inspection of the plot shows that this is the case. FIG. 10B is a sample response obtained after treatment with beads containing anti-IgG:anti-IgM immunoglobulins. This treatment is also removes both paraprotein responses. FIG. 10C is a sample response obtained after treatment with beads containing an anti-kappa light chain. This treatment removes the paraprotein at −0.07 normalized mobility units as well as a large amount of the "normal" response, but does not remove the paraprotein at −0.12 normalized mobility units. FIG. 10D is a sample response obtained after treatment with beads containing an anti-lambda light chain. This treatment removes the paraprotein at −0.12 normalized mobility units, but does not subtract the paraprotein at −0.07 normalized mobility units.

Figure 11A:
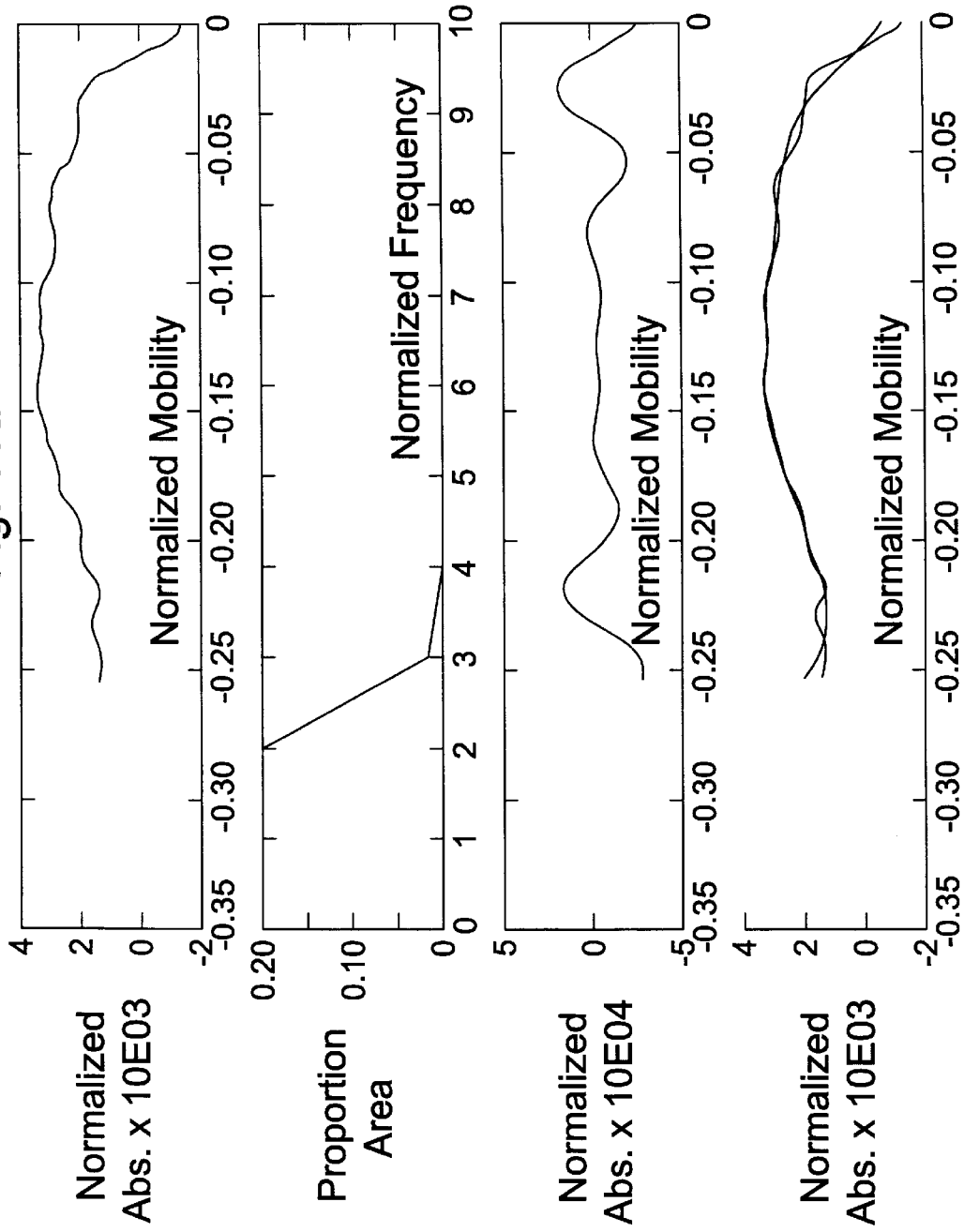
FIGS. 11A–D are a set of four graphs which provide an illustration of the Fourier Analysis results from each of the individual sample treatments from FIGS. 10A–D.
Figure 11B:
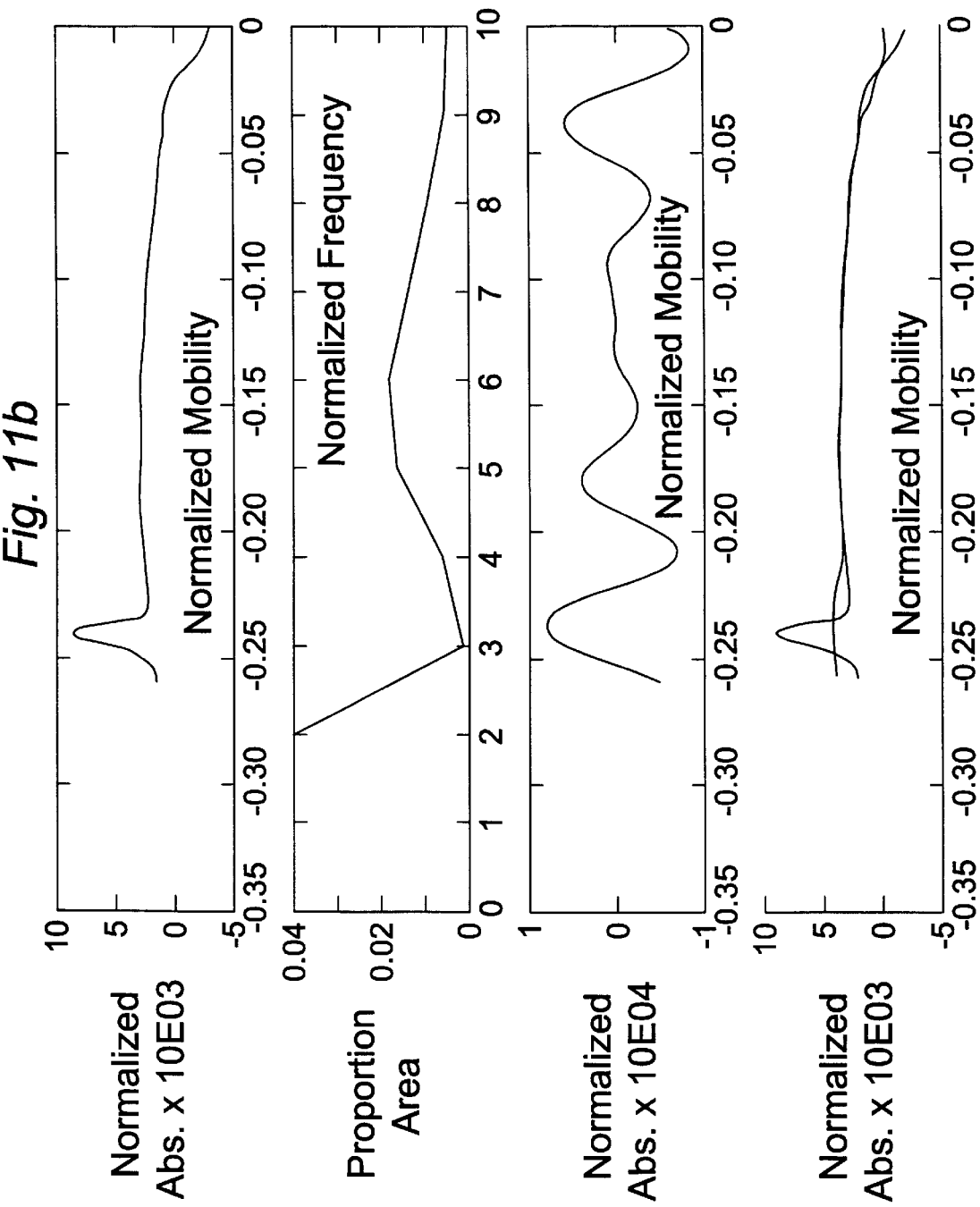
Figure 11C:
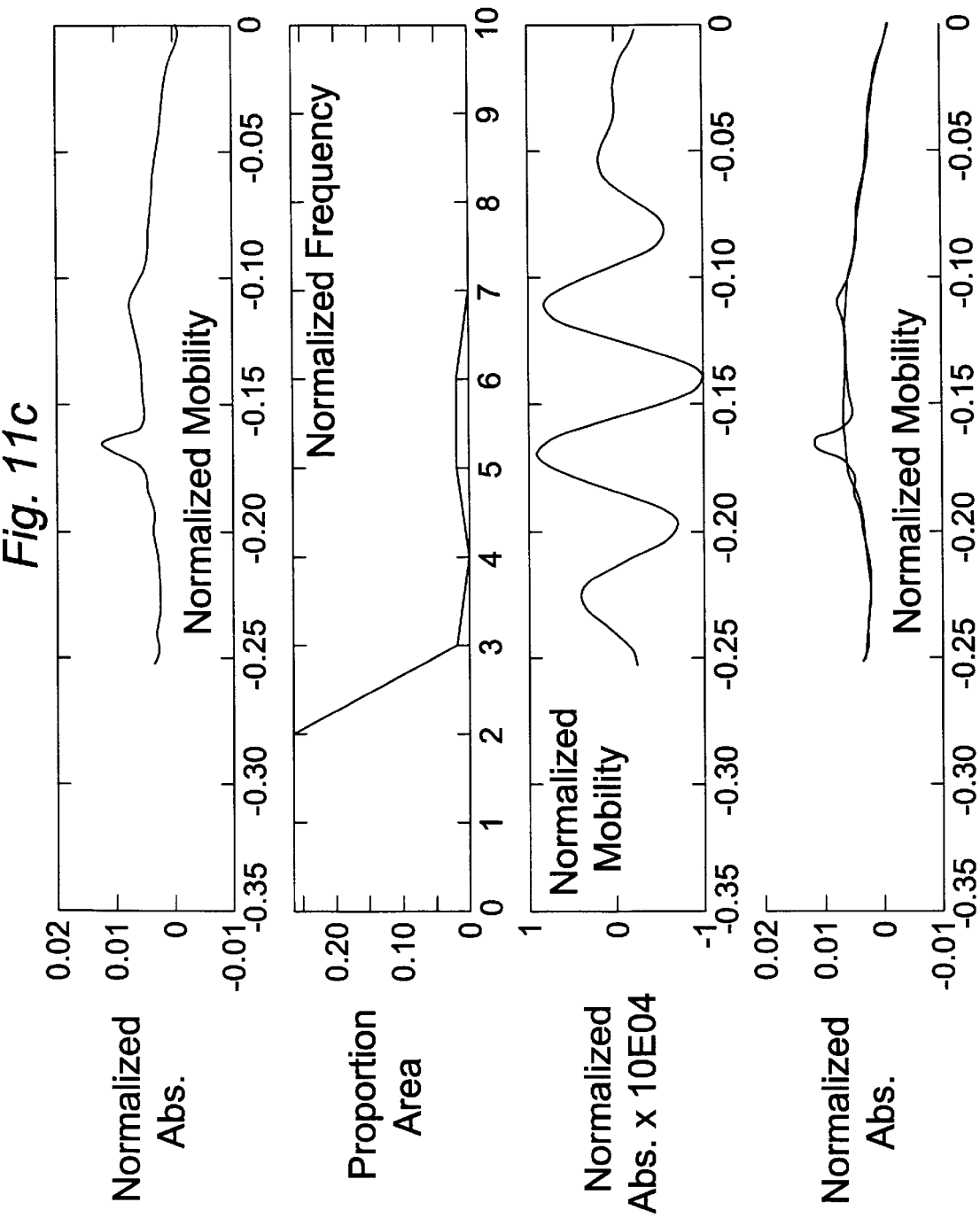
Figure 11D:
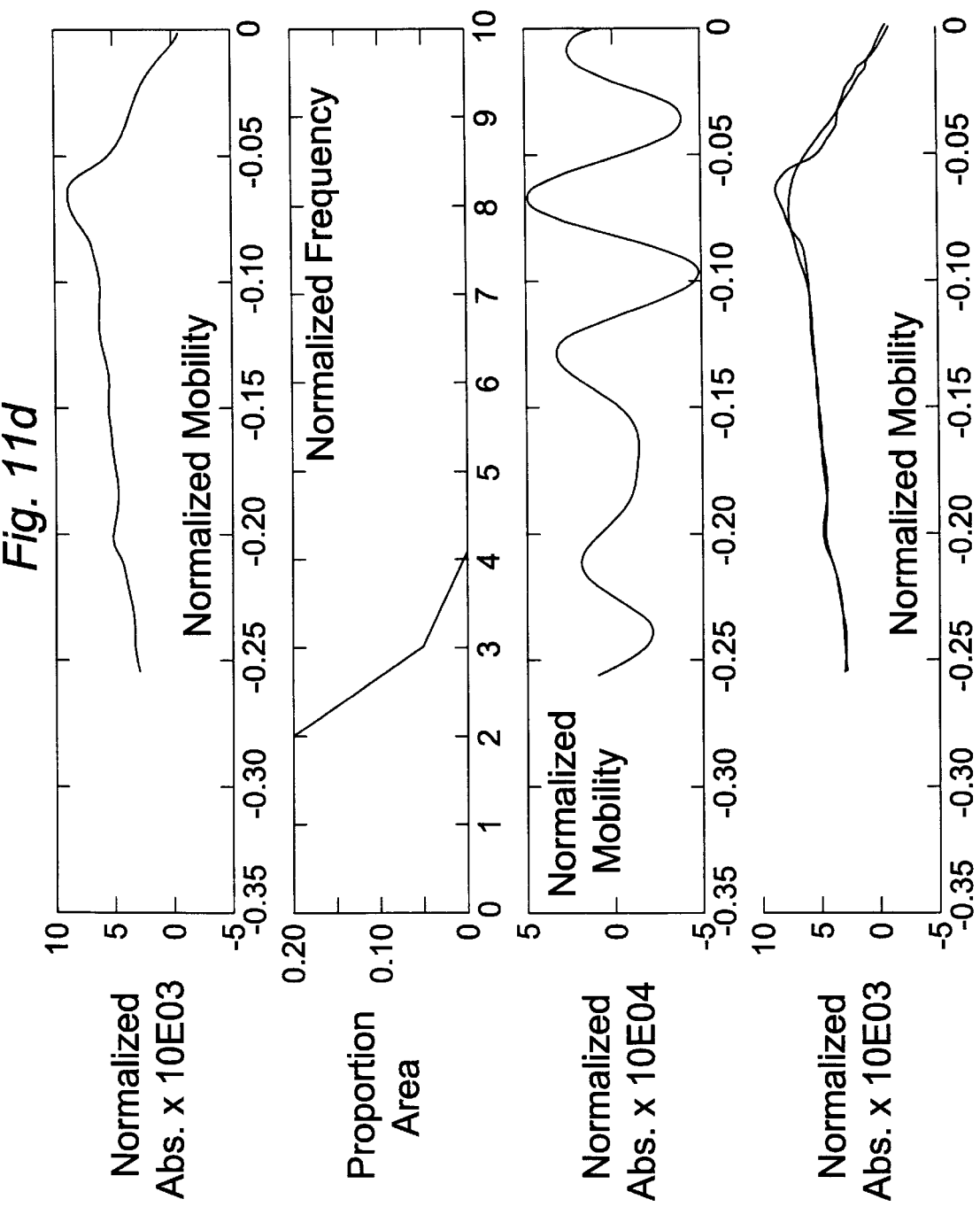

FIGS. 11A–D are a set of four graphs which provide an illustration of the Fourier Analysis results from each of the individual sample treatments. The top subplot in FIGS. 11A–D shows the final result of the analysis for each of the four panel samples. The only feature found in FIG. 11A results from a spike of undetermined origin. No paraprotein response is found in FIG. 11B. FIG. 11C again finds the spike of undetermined origin, along with the paraprotein at normalized mobility −0.12. FIG. 11D finds the spike of undetermined origin, and the paraprotein at normalized mobility −0.07. The second subplot in FIGS. 11A–D shows the power spectrum generated, with proportion area specifically being plotted in this instance. The third subplot in FIGS. 11A–D represents the back-transform of the data in the first subplot after it has been filtered to exclude the non-characteristic frequency part. The fourth subplot in FIGS. 11A–D is a comparison between the original data and a back-transform of the non-characteristic frequency part of the data.

FIG. 12 is the result obtained by running this sample panel through the method of the present invention. The correct feature locations were input to the algorithm. The method correctly identified the identity of the component at −0.07 normalized mobility units as IgG, kappa, and the identity of the component at −0.12 normalized mobility units as IgG, lambda. Feature 1 Analysis: Treatments 1 and 2 yield check region results of negative no paraproteins found, and are assigned the value low (−). Treatment 3 yields a check result of positive (+), but no valid feature is found by the check region algorithm in the vicinity of −0.0700 normalized mobility units, so the sample result is also low (−). Treatment 4 yields a check region result of 1, and a valid feature is found by the check region algorithm in the vicinity of −0.0700 normalized mobility units, giving a high (+) result for this treatment. This set of panel results [−,−,−,+] yield the correct result for Feature 1: IgG, Kappa. Feature 2 Analysis: Treatments 1 and 2 yield check region results of negative (−), no paraproteins found, and are assigned the value low (−). Treatment 3 yields a check result of positive (+), and a valid feature is found by the check region algorithm in the vicinity of −0.1200 normalized mobility units, giving a high (+) result for the sample. Treatment 4 yields a check result of positive (+), but no valid feature is found by the check region algorithm in the vicinity of −0.12 normalized mobility units, giving a low (−) result for this treatment. This set of panel results [−,−,+,−] yield the correct result for Feature 2: IgG, Lambda.

All publications, patents and patent applications mentioned in this specification are herein incorporated by reference into the specification to the same extent as if each individual publication, patent or patent application was specifically and individually indicated to be incorporated herein by reference.

Although the invention has been described with reference to preferred embodiments and examples thereof, the scope of the present invention is not limited only to those described embodiments. As will be apparent to persons skilled in the art, modifications and adaptations to the above-described invention can be made without departing from the intent and scope of the invention, which is defined and circumscribed by the appended claims.

What is claimed is:

1. An immunosubtraction method of analyzing a biological sample for the presence or absence of at least one constituent of interest, said method comprising:

(a) admixing at least one aliquot of said biological sample with at least one specific binding partner, said at least one specific binding partner capable of significantly removing said at least one constituent of interest to generate a first treated sample;

(b) separating a portion of said first treated sample into constituent parts to generate a first data set;

(c) subjecting at least a portion of said first data set to a first analysis to generate a parameter set indicative of said at least one constituent of interest;

(d) assigning a binary decision code to said first treated sample using said parameter set; and (e) comparing said binary decision code to a matrix of expected results to identify said constituent of interest.

2. An immunosubtraction method of analyzing a biological sample of claim 1, wherein said biological sample is a member selected from the group consisting of serum, blood, plasma, urine and cerebrospinal fluid.

3. An immunosubtraction method analyzing a biological sample of claim 1, wherein said at least one constituent of interest comprises a protein.

4. An immunosubtraction method of analyzing a biological sample of claim 1, wherein said at least one constituent of interest comprises an immunoglobulin.

5. An immunosubtraction method of analyzing a biological sample of claim 4, wherein said immunoglobulin is a member selected from the group consisting of IgG, IgA, IgM, IgD, IgE, kappa, lambda and mixtures thereof.

6. An immunosubtraction method of analyzing a biological sample of claim 8, wherein said at least one constituent of interest is present at a level of about 50 mg/dL to about 1000 mg/dL.

7. An immunosubtraction method of analyzing a biological sample of claim 1, wherein said at least one constituent of interest comprises a paraprotein.

8. An immunosubtraction method of analyzing a biological sample of claim 1, wherein said at least one constituent of interest is present at a level of about 50 mg/dL to about 10,000 mg/dL.

9. An immunosubtraction method of analyzing a biological sample of claim 1, wherein said at least one specific binding partner is an antibody.

10. An immunosubtraction method of analyzing a biological sample of claim 9, wherein said antibody is a member selected from the group consisting of anti-IgG, anti-IgA, anti-IgM, anti-IgD, anti-IgE, anti-kappa, anti-lambda, protein G and mixtures thereof.

11. An immunosubtraction method of analyzing a biological sample of wherein said biological sample is admixed with two of said at least one specific binding partner.

12. An immunosubtraction method of analyzing a biological sample of claim 1, wherein said at least one aliquot is four aliquots, said four aliquots designated aliquot 1, aliquot 2, aliquot 3 and aliquot 4.

13. An immunosubtraction method of analyzing a biological sample of claim 12, wherein said aliquot 1 is treated with a mixture of anti-IgG:anti-IgA; said aliquot 2 is treated with a mixture of anti-IgG:anti-IgM; said aliquot 3 is treated with anti-kappa; and said aliquot 4 is treated with anti-lambda.

14. An immunosubtraction method of analyzing a biological sample of claim 1, wherein said at least one specific binding partner is attached to a solid support.

15. An immunosubtraction method of analyzing a biological sample of claim 14, wherein said solid support is a member selected from the group consisting of a gel, a bead and a microparticle.

16. An immunosubtraction method of analyzing a biological sample of claim 1, wherein said separation is accomplished by electrophoresis.

17. An immunosubtraction method of analyzing a biological sample of claim 16, wherein said electrophoresis is capillary electrophoresis.

18. An immunosubtraction method of analyzing a biological sample of claim 16, wherein said capillary electrophoresis is zone capillary electrophoresis.

19. An immunosubtraction method of analyzing a biological sample of claim 1, wherein said first data set is a delimited mobility data set.

20. An immunosubtraction method of analyzing a biological sample of claim 1, wherein said first data set is a delimited mobility data set which is mobility zero corrected and normalized.

21. An immunosubtraction method of analyzing a biological sample of claim 1, wherein said first data set is a time data set.

22. An immunosubtraction method of analyzing a biological sample of claim 1, wherein said first analysis is a check analysis, said check analysis comprising:
  (i) subjecting at least a portion of said first data set to Fourier transform to generate forward-transformed data sets;
  (ii) finding a proportion area of a characteristic frequency region, and an area of said characteristic frequency region;
  (iii) selecting any forward-transformed data sets having a characteristic frequency component above a first preselected threshold;
  (iv) filtering and back-transforming data sets selected in step (iii) to provide filtered back-transformed data sets;
  (v) identifying the magnitude and location of residual maxima in the filtered, back-transformed data sets;
  (vi) comparing the location of said residual maxima having a magnitude above a second preselected threshold to a corresponding location in the first data set; and
  (vii) finding the position and magnitude of any found feature to detect the presence of a constituent of interest and forming a parameter set indicative of said constituent of interest.

23. An immunosubtraction method of analyzing a biological sample of claim 22, wherein said check analysis results in a parameter set indicative of said constituents of interest, said parameter set being members selected from the group consisting of signal proportion, signal amount, presence of signal and residual, and combinations thereof.

24. An immunosubtraction method of analyzing a biological sample of claim 1, wherein said first analysis is a software scan analysis.

25. An immunosubtraction method of analyzing a biological sample of claim 1, wherein said binary decision code is assigned by comparing said parameter set to criteria which are members selected from the group consisting of the presence of a suspect feature, the proportion of signal, the amount of signal and the amount of residual.

26. An immunosubtraction method of analyzing a biological sample of claim 25, wherein said parameter set is derived from a region which is a member selected from the group consisting of gamma region, beta region, C-3, transferrin, alpha 1 and alpha 2 region.

27. An immunosubtraction method of analyzing a biological sample of claim 1, wherein said first treated sample is generated from at least two specific binding partners.

28. An immunosubtraction method of analyzing a biological sample of claim 1, wherein said matrix of expected results comprises a predetermined set of binary decision codes.

29. An immunosubtraction method of analyzing a human serum sample for the presence or absence of at least one paraprotein, said method comprising:
  (a) admixing at least one aliquot of said sample with at least one binding partner, said binding partner capable of significantly removing said at least one paraprotein to generate a first treated sample;
  (b) separating a portion of said first treated sample into constituent parts by capillary electrophoresis to generate a first data set;
  (c) subjecting at least a portion of said first data set to a first analysis to generate a parameter set indicative of said constituent of interest;
  (d) assigning a binary decision code to said first treated sample using said parameter set; and
  (e) comparing said binary decision code to a matrix of expected results to identify said paraprotein.

30. A method of claim 29, wherein said at least one binding partner is a member selected from the group consisting of anti-IgG:anti-IgA, anti-IgG:anti-IgM, anti-kappa, anti-lambda and mixtures thereof.

31. A method of claim 29, wherein said first analysis is a check analysis comprising:
  (i) subjecting at least a portion of said first data set to Fourier transform to generate forward-transformed data sets;
  (ii) finding a proportion area of a characteristic frequency region, and an area of said characteristic frequency region;
  (iii) selecting any forward-transformed data sets having a characteristic frequency component above a first preselected threshold;
  (iv) filtering and back-transforming data sets selected in step (iii) to provide filtered, back-transformed data sets;
  (v) identifying the magnitude and location of residual maxima in the filtered, back-transformed data sets;
  (vi) comparing the location of said residual maxima having a magnitude above a second preselected threshold to a corresponding location in the first data set; and
  (vii) finding the position and magnitude of any found feature to detect the presence of said paraprotein by forming a parameter set indicative of said paraprotein.

32. A method of claim 29, wherein said parameter set are members selected from the group consisting of proportion of paraprotein frequency signal, amount of paraprotein frequency signal, presence and magnitude of paraprotein peaks and residual.

33. A method of claim 32, wherein said decision of a binary code is assigned to said first treated sample by comparing said parameter set to criteria which are members selected from the group consisting of the presence and magnitude of a suspect feature, the proportion of signal at paraprotein frequencies, the amount of signal at paraprotein frequencies and amount of residual.

34. A method of claim 33, wherein said binary decision code is assigned from at least two specific binding partners.

35. A method of claim 29, wherein said at least one aliquot is four aliquots, said four aliquots designated aliquot 1, aliquot 2, aliquot 3 and aliquot 4.

36. A method of claim 35, wherein said aliquot 1 is treated with a mixture of anti-IgG:anti-IgA; said aliquot 2 is treated with a mixture of anti-IgG:anti-IgM; said aliquot 3 is treated with anti-kappa; and said aliquot 4 is treated with anti-lambda.

* * * * *